United States Patent [19]

Golen et al.

[11] Patent Number: 5,318,487

[45] Date of Patent: Jun. 7, 1994

[54] EXERCISE SYSTEM AND METHOD FOR MANAGING PHYSIOLOGICAL INTENSITY OF EXERCISE

[75] Inventors: Emil S. Golen, Barrington; Gary E. Oglesby, Manhattan, both of Ill.; Donald J. Alexander, Milwaukee, Wis.

[73] Assignee: Life Fitness, Franklin Park, Ill.

[21] Appl. No.: 881,918

[22] Filed: May 12, 1992

[51] Int. Cl.[5] .......................................... A63B 21/005
[52] U.S. Cl. ........................................ 482/5; 482/3; 482/8; 482/900; 482/902; 73/379.01
[58] Field of Search .................. 482/1, 3-9, 482/51-54, 57, 900-903; 128/25 R, 25 B; 73/379.01, 379.06, 379.07; 364/413.04, 550; 340/762, 765, 784, 782; 345/46, 50

[56] References Cited

U.S. PATENT DOCUMENTS

| | | |
|---|---|---|
| 3,395,698 | 8/1968 | Morehouse . |
| 3,744,480 | 7/1973 | Gause et al. . |
| 4,112,928 | 9/1978 | Putsch . |
| 4,244,021 | 1/1981 | Chiles, III . |
| 4,278,095 | 7/1981 | Lapeyre ............................ 482/7 X |
| 4,436,097 | 3/1984 | Cunningham . |
| 4,678,182 | 7/1987 | Nakao et al. . |
| 4,817,938 | 4/1989 | Nakao et al. . |
| 4,911,427 | 3/1990 | Matsumoto et al. . |
| 4,919,416 | 4/1990 | DeCloux ........................ 482/901 X |
| 4,934,692 | 6/1990 | Owens . |
| 4,976,424 | 12/1990 | Sargeant et al. . |
| 5,001,632 | 3/1991 | Hall-Tipping ................. 482/902 X |
| 5,018,726 | 5/1991 | Yorioka ....................... 73/379.06 X |
| 5,067,710 | 11/1991 | Watterson et al. . |
| 5,104,120 | 4/1992 | Watterson et al. . |

Primary Examiner—Richard J. Apley
Assistant Examiner—Joe H. Cheng
Attorney, Agent, or Firm—Michael B. McMurry

[57] ABSTRACT

An exercise management system is disclosed for maintaining a user's level of exercise intensity (such as measured by heart rate) at a target level while exercising. In one embodiment, the system includes a movement member (such as pedals) which is engaged by the user to provide an exercise movement. The movement member is selectively adjustable to varying the intensity of exercise performed by the user. A heart rate sensor indicates the user's heart rate, and a computer adjusts the movement member in accordance with the heart rate signal to establish and maintain the user's heart rate near the target level. The user may periodically disengage the heart rate sensor for a limited time, during which time the computer maintains the user's heart rate near the target level by adjusting load in accordance with the user's rate of exercise (such as measured by rpm).

47 Claims, 12 Drawing Sheets

EXERCISE SYSTEM AND METHOD FOR MANAGING PHYSIOLOGICAL INTENSITY OF EXERCISE

FIELD OF THE INVENTION

This invention relates to aerobic exercise equipment, and more particularly to exercise equipment with loads which are variable for maintaining a user's heart rate or other physiological condition at a predetermined level.

BACKGROUND OF THE INVENTION

Exercise generally, and aerobic exercise in particular, is of value to individuals because it conditions and improves respiratory and circulatory systems. Exercise is characterized in part by intensity and duration. Intensity, which may be thought of as the effort expended by an individual, is reflected in the individual's physiological condition. For example, heart rate, breathing and metabolism increase with exercise intensity, and are referred to herein as the "physiological indicators of intensity."

While exercise intensity is a physiological phenomenon and is properly measured by one of the physiological indicators, it is also manifested outside the body by an individual's physical movement or by the physically measurable work performed by the individual. For example, at a fixed level of resistance, pedal rpm on stationary exercise bicycle gives some indication of the individual's level of exercise intensity. This type of indication is referred to herein as an externally observable "physical indicator of intensity."

While physical indicators of intensity such as ergometers or tachometers are easier to implement than physiological indicators of intensity, their usefulness is limited because of the subjective nature of exercise. For example, two persons riding a stationary bicycle at the same levels of speed and resistance would appear to have the same level of exercise intensity based externally observable physical indicators, such as pedal rpm. Depending upon each person's level of fitness, their respective actual levels of exercise intensity (as measured by one of the physiological indicators) could be quite different.

For effective aerobic exercise, it is necessary that physiological intensity reach a certain minimum threshold. At the same time, if exercise is too intense, it becomes primarily anaerobic (i.e., oxygen depleting). Exercise at an excessive level of intensity does not yield additional improvements in the body's aerobic fitness.

Thus, between the upper and lower thresholds of training intensity lies the aerobic training range. It is important, therefore, to monitor levels of intensity to ensure that intensity falls within this training range. To monitor intensity, a number of physiological conditions may be inspected, including heart rate, breathing as a percentage of maximal oxygen intake, and metabolism.

Typically, such monitoring requires a sensor which is placed in physical contact with an individual to measure the individual's heart rate or the like. The individual can then be apprised of his or her level of exercise intensity. One simple example of this is someone on a stationary exercise bicycle who takes his or her own pulse after a workout to determine whether he or she has reached a sufficient level of aerobic intensity.

A more sophisticated approach, however, is to employ biofeedback techniques for periodically adjusting workout intensity in response to the physiological indicators of intensity, such as heart rate. Examples of such devices are provided in U.S. Pat. Nos. 3,395,698 and 3,744,480. While theoretically any of the physiological indicators may be used, it is most practical to use heart rate, and therefore the examples set forth herein all use heart rate as the physiological indicator of intensity.

Devices which employ biofeedback techniques include exercise bicycles having variable load resistance to pedal movement. This resistance can be provided by well-known mechanical and electrical devices, including alternators, which can be coupled by chains or belts to the pedals.

In such devices, a heart rate detector is coupled to the user, typically by an ear clip. A target heart rate is selected, either by the user or automatically by the device. As the user exercises, his or her pulse is periodically measured and compared to the target heart rate. If the user's heart rate is below the target, the load resistance is increased. Likewise, if the user's heart rate is above the target heart rate, the load resistance is decreased.

In this manner, these exercise devices function as "biofeedback-type systems." They adjust load resistance as a function of heart rate to establish and maintain the user's heart rate (i.e., physiological exercise intensity) at or near the desired or target level. For a variety of reasons, these devices have been less than optimal.

Specifically, for effective operation, these systems depend on the continuous availability of heart rate data. For example, if the user wears an ear clip, heart rate data is available throughout the exercise.

There have, however, been recent advances in heart rate detection technology, such as disclosed in U.S. patent application Ser. No. 07/722,800 filed Jun. 28, 1991 (assigned to the assignee of this application) and incorporated herein by reference. Unlike older heart rate detection techniques which required cumbersome ear clips or the like, this new detection technology measures a user's heart rate whenever his or her hands are placed on the exercise device's handgrips. Such handgrips, for example, can be located on the handlebars of an exercise bicycle.

One disadvantage, however, of locating the detectors on the handgrips in a heart rate measurement system is that the user will tend to remove his hands from the handgrips from time to time. When the user's hands are removed, the biofeedback-type device will receive no information about the user's heart rate. To be practical, a heart rate management system should continue to operate effectively even when the flow of heart rate data is interrupted for periods as long as ninety seconds. Existing systems are not designed to handle the intermittent availability of heart rate signals.

Moreover, it has come to be appreciated that systems should not only be able to process intermittent heart rate data, but in fact periodically should also invite users to remove their hands from the handgrips (or otherwise disengage the sensor). In this manner, the user does not feel "chained" to the heart rate measuring device, and is free to wipe his or her brow, turn the pages of a book, adjust a personal tape player, or do any of the many things people riding an exercise bicycle are likely to do to divert their attention from an otherwise boring exercise.

As explained above, externally observable indicators of exercise intensity (such as pedal speed) are related to the user's actual physiological level of exercise intensity, but are of limited value as tools for measuring that intensity because they are not calibrated for each individual user. Consequently, biofeedback-type devices of the past have relied on heart rate, and have not utilized external indicators (such as pedal rpm) in conjunction with physiological data to attain the highest possible performance.

Also, in some existing devices, load changes tend to be too abrupt and too frequent. Preferably, for most people load changes should be gradual. On the other hand, it may be desirable to make load changes more dramatic for persons in better physical condition. It is also desirable that the device should anticipate changes in the user's heart rate so that load can be adjusted earlier, and therefore more gradually.

SUMMARY OF THE INVENTION

The present invention provides an exercise system and method for managing the physiological intensity of exercise. The system and method are not only very effective, but also allow the user the comfort and convenience of being able to periodically disengage himself or herself from the pulse sensor and to exercise at various speeds. Moreover, devices built in accordance with the invention continue to operate effectively even when the signal representing heart rate is interrupted for periods as long as ninety seconds. The invention uses externally observable physical indicators of exercise intensity such as pedal rpm in conjunction with physiological indicators such as heart rate for improved control over exercise intensity.

In one embodiment of the invention, an exercise apparatus such as a stationary bicycle is provided for establishing and maintaining a user's heart rate near a target heart rate during exercise The apparatus includes pedals or other suitable members which are manipulated by the user in an exercise movement. A load device opposes the movement of the pedals with selectable levels of resistance. Thus, the difficulty of pedaling is adjustable to vary the intensity of exercise.

A sensor, preferably located on the bicycle's handlebars, detects the user's heart rate, while a tachometer measures the speed at which the user pedals. An internal computer or other suitable control circuit is connected to the sensor, tachometer and load device. A control panel, also connected to the computer, provides the user with a display of information, including heart rate, rpm and load level. A keyboard on the control panel enables the user to enter information such as his or her age or desired target heart rate.

During the initial portion of the exercise, the computer reads the user's heart rate, and adjusts the load device to make pedaling harder or easier in order to establish and maintain the user's heart rate near the target level. For example, if the user's heart rate were below the target heart rate and were not increasing, then the computer would adjust the load device to make pedaling more difficult, thereby tending to increase the user's heart rate.

Once the user has attained the target heart rate, the computer invites the user from time to time to disengage the sensor by taking his or her hands off the handlebars for a limited time period. This allows the user freedom to use his or her hands during exercise without being "chained" to the sensors. The time limit which the user is allowed to keep his or her hands off the sensors is determined by the computer based on recent changes in the user's heart rate.

When the user's hands are removed from the sensors, the computer continues to maintain the user's heart rate near the target based on changes in the user's rpm level. In this manner, the computer uses pedal rpm (a physical indicator of exercise intensity) to supplement heart rate (a physiological indicator of exercise intensity). The computer adjusts load resistance in accordance with pedal rpm to maintain the user's heart rate near the target.

Specifically, if the user pedals faster over time, the computer reduces the load resistance to anticipate the increase in the user's heart rate. Conversely, if the user pedals slower, the computer increases load resistance to anticipate the decrease in the user's heart rate.

As discussed above, rpm alone does not provide a valid indication of an individual user's true level of physiological intensity. We have realized, however, that externally observable physical indicators such as rpm do have value in managing physiological exercise intensity when used in conjunction with the physiological indicators such as heart rate.

Thus, once the heart rate sensor indicates that the user has attained the target heart rate, the computer uses pedal rpm to supplement information received from the heart rate sensor, particularly during times when heart rate data is unavailable (such as when the user's hands are off of the heart rate sensors). Even when the user's hands are on the sensors, the computer uses pedal rpm to anticipate changes in heart rate. By anticipating changes in heart rate, load adjustments can be made more gradual, and the heart rate more steady.

When the computer requires fresh heart rate data, it prompts the user via a visual display to place his or her hands on the sensors. If the user fails to do so within a predetermined amount of time, the computer initiates a warning signal, such as a bell. If the user continues to ignore the prompt, the computer substantially reduces the load resistance. This encourages the user to place his hands on the sensors, as well as deters the user from exercising beyond his aerobic level.

The invention may also be embodied in a kit comprising sensors, controllers and computers, which could be sold separably for upgrading existing exercise devices.

It is, therefore, an object of the invention to provide an exercise intensity management system and method which does not require the user to remain constantly coupled to a heart rate measuring device. Moreover, the system actually invites the user to release or disengage the measuring device, and then periodically prompts the user to re-engage the measuring device as necessary.

It is an additional object of the present invention to provide an exercise management system which adjusts the load resistance of the exercise device in response to changes in the user's rate of exercise (or other externally observable physical indicator) as well as the user's heart rate.

DETAILED DESCRIPTION OF THE INVENTION

A. Technical Environment

In the present invention, a biofeedback-type heart rate management system is provided which provides new, useful features and superior performance.

Figure 1:
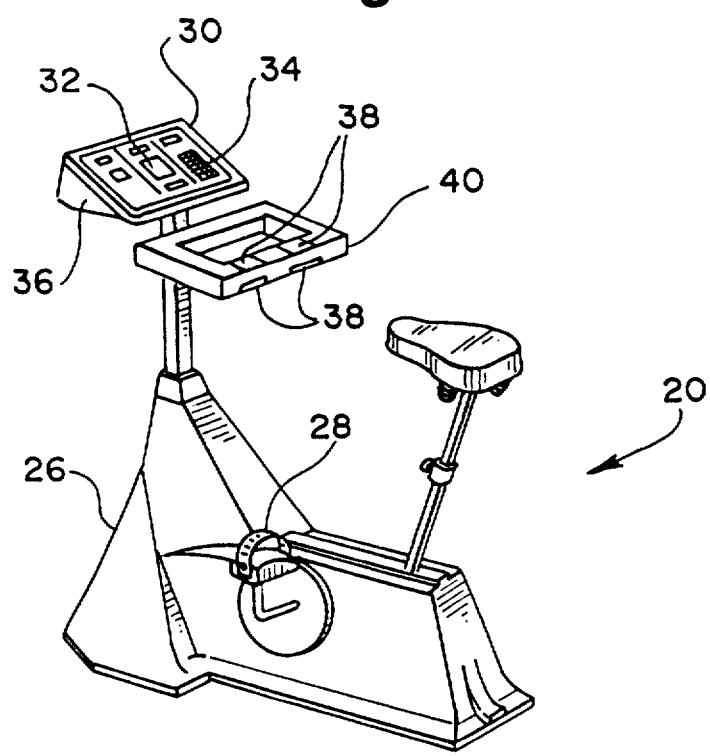
FIG. 1 is a perspective view of an exercise bicycle in accordance with one embodiment of the invention.
Figure 2:
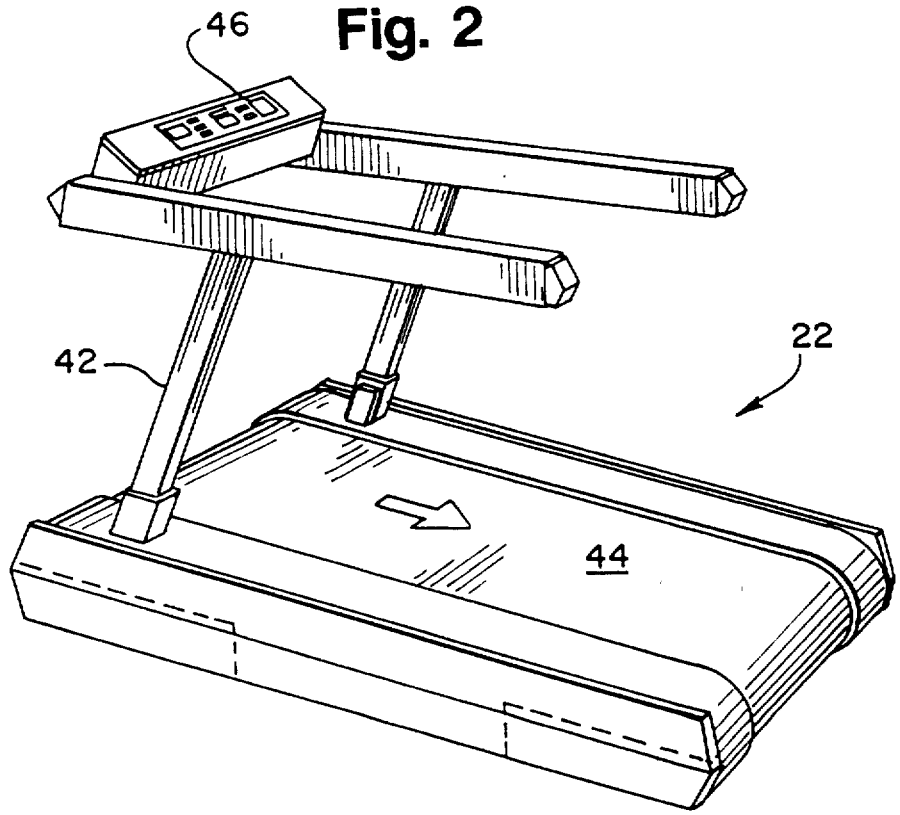
FIG. 2 is a perspective view of a exercise treadmill in accordance with one embodiment of the invention.
Figure 3:
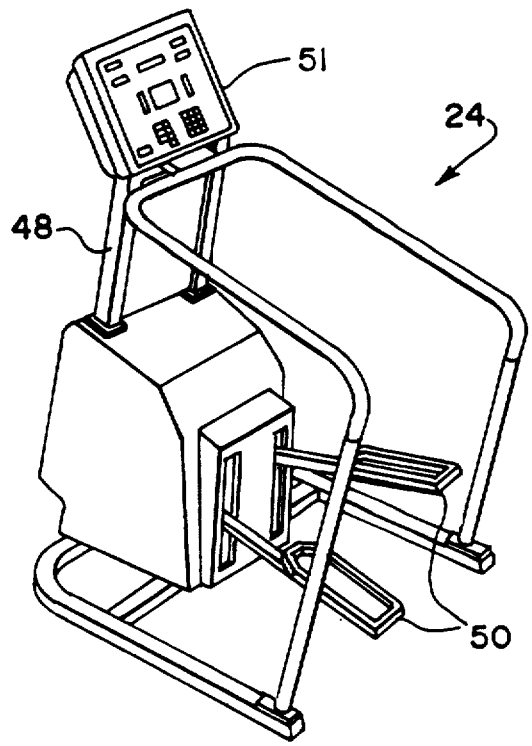
FIG. 3 is a perspective view of an exercise machine for simulating stair climbing in accordance with one embodiment of the invention.

Referring to FIGS. 1, 2 and 3, computer-controlled exercise devices 20, 22, and 24 employing one embodiment of the invention are illustrated. Except for the aspects of the invention described herein, each of the devices 20, 22 and 24 is well-known and commercial available from suppliers such as the Life Fitness of Franklin Park, Ill.

The device 20 is a typical exercise bicycle, and includes a frame 26 on which a user may sit. The user exercises by manipulating pedals 28 in an exercise movement. A resistance load device (not illustrated in FIG. 1) is housed within the frame 26 and is coupled to the pedals 28 by a belt, chain or the like. The load device provides a selectively variable resistance to the movement of the pedals 28. The load device may be mechanical or electromechanical. One example of such a device is provided in U.S. Pat. No. 4,817,938 issued Apr. 4, 1989.

A control panel 30 includes a data display 32 and a keypad 34 which enables communication between an internal computer and the user. The internal computer generates a load control signal, which is coupled to the variable load resistance device. Thus, a user may select a particular load level via the keypad 34. The internal computer then generates the appropriate load control signal.

The bicycle 20 also includes a heart rate monitor 36, which is preferably the heart rate detection system disclosed in U.S. patent application Ser. No. 07/722,800, filed Jun. 28, 1991. The monitor 36 includes four electrodes or "biopotential sensors" 38 which are mounted on a handlebar 40 of the bicycle 20. To engage the monitor 36, a user riding the bicycle 20 touches the electrodes 38 with the palms and fingers of his hands.

Referring to FIG. 2, the device 22 is a typical treadmill, which includes a frame 42 having an endless belt 44 upon which a user runs or walks. The movement of the belt 44 serves the same function as the movement of pedals 28 in bicycle 20. The treadmill 22 also includes a motor which is housed within the frame 42 and is coupled to belt 44. The motor, under computer control, drives the belt 44 at a predetermined rate. One example of such a device is provided in U.S. patent application Ser. No. 07/686,906 filed Apr. 17, 1991 and assigned to the assignee of this application.

As described above in connection with the bicycle 20, the treadmill 22 also includes a control panel 46 which enables communication between a computer and the user. The computer or user generates a speed control signal that controls the speed of the belt 44 of the treadmill 22. The computer also generates an incline control signal which allows the belt 44 to be selectively placed on an incline relative to the horizontal. The steeper the incline, the more intense a user's exercise at a given belt speed. Thus, the incline functions as a load resistance device for providing a selectively variable resistance to the user's exercise movement. The treadmill 22 also includes a heart rate monitor such as the heart rate monitor 36 of the bicycle 20 (not illustrated).

Referring to FIG. 3, device 24 is a typical stair climbing simulating machine which includes a frame 48 having vertically reciprocating pedals 50 upon which a user stands to simulate an aerobic stair climbing movement. One example of such a device is provided in U.S. patent application. Ser. No. 07/658,156 filed Feb. 20, 1991 and assigned to the assignee of this application. The movement of the pedals 50 serves a comparable function as the movement of the pedals 28 in bicycle 20 and belt 44 in treadmill 22. The stair machine 24 also includes a resistance load device which is housed within the frame 48 and is coupled to the pedals 50. The load device provides a selectively variable resistance to the movement of the pedals 50. The load device may be mechanical or electromechanical, and functions to increase the user's exercise intensity. Alternatively, the load device could vary the vertical distance which the pedals 50 reciprocate to provide greater exertion per step.

As described above in connection with the bicycle 20, the stair climbing machine 24 also includes a control panel 51 which enables communication between an internal computer and the user. The computer generates a load control signal, which is coupled to the variable load resistance device. The device 24 also includes a heart rate monitor (not illustrated in FIG. 3) such as the heart rate sensor monitor 36 of the bicycle 20.

As will be apparent, biofeedback-type devices employing the present invention may take a number of forms, including that of each of the devices 20, 22 and 24. Each of these devices includes a movable member such as pedals 28 or belt 44 which provides the user with an exercise movement The manipulation can be by hand or foot, and may be circular, reciprocating and so forth. Each device also includes a mechanism for controlling the rate or resistance of the exercise. This mechanism is selectively adjustable to vary the exercise intensity experienced by the user. Throughout this application, we refer to such devices as load devices, but it will be understood that the term load device contemplates any apparatus (such as those described above) which can be used to increase or decrease the intensity of the user's exercise.

Each device 20, 22 and 24 also includes a pulse monitor along with analog or digital processing circuits for comparing the heart rate measured by the pulse sensor to a predetermined or target heart rate. As explained above, heart rate is but one of the physiological indicators of exercise intensity, and for convenience it is used in the foregoing illustrations. It should be understood that the monitors could measure other physiological indicators.

Finally, each device 20, 22 and 24 is equipped with a rate sensor (not shown in FIGS. 1-3) measuring rate of exercise activity (e.g., pedal rpm). It will be recalled from the Background discussion that phenomenon such as pedal speed which are observable outside the body are some indication of the user's exercise intensity, and are referred to as externally observable physical indicators of intensity. They can be thought of as rough approximations of true physiological intensity, which is best measured by a physiological indicator such as heart rate.

Because exercise movements in the devices 20, 22 and 24 tend to be repetitive, it is helpful to describe these movements in terms of revolutions or cycles per second. For example, on the exercise bicycle 20, the user exercises by rotating the pedals 28. The rate of exercise is simply the rate at which the pedals 28 rotate, and is expressed in revolutions per minute (rpm). It will be understood that references herein to rpm contemplate not only any measure of the cycles per second of repetitive exercise movements (such as stair climbing) but also the broader concept of externally observable physical indicators of exercise intensity.

B. General Operation of the Invention

For simplicity, the operation of the invention is explained with respect only to the bicycle 22. It is understood that in bicycle 20 pedal rpm is used as the externally observable physical indicator of exercise intensity. In accordance with the invention, bicycle 20 maintains the user's heart rate (or other physiological indicator of exercise intensity) near a target level by adjusting load resistance in response to the user's heart rate. The bicycle 20 can maintain the user's heart rate near the target level even when heart rate data is unavailable for limited time periods. Once the user has reached the target heart rate, the bicycle 20 also uses pedal rpm to supplement the information it receives about heart rate.

In the preferred embodiment, the user begins an exercise session by entering his age on the keyboard 34 of control panel 30. The system then computes a target heart rate based on the user's age in accordance with any suitable formula. Alternatively, the user may designate a target heart rate. The user then enters an initial load level.

The bicycle 20 then sets load resistance at the user-selected load level for a three-minute warm-up period. At the conclusion of the warm-up period, the bicycle 20 prompts the user with data display 32 to place his hands on the heart rate sensors 38. When the user's hands are placed on the sensors 38, the user's heart rate is displayed on the data display 32, and the heart rate monitor 36 begins to periodically sample the user's heart rate. Bicycle 20 adjusts the load in accordance with the user's heart rate to establish the user's heart rate near the target.

Once the user has reached or exceeded the target heart rate, the bicycle 20 begins to use pedal rpm (a physical indicator of exercise intensity) to supplement heart rate (a physiological indicator of exercise intensity). Thus, if the user increases pedal rpm, the bicycle 20 reduces load resistance to anticipate the user's increase in heart rate. Conversely, if the user decreases pedal rpm, the bicycle 20 increases load resistance to anticipate the user's decreasing heart rate.

As discussed above, physically-based indicators of exercise intensity (such as pedal rpm) do not by themselves provide valid indications of an individual user's true level of physiological intensity. We have realized, however, that physically-based indicators do have value in managing physiological exercise intensity when used in conjunction with the physiological indicators.

In the case of bicycle 20, heart rate is used to measure physiological exercise intensity, and pedal rpm is used to measure physical level of exercise intensity. Once the user has reached the target heart rate, the user's heart rate is closely related to the user's pedal rpm. In effect, what was formerly data of limited value (i.e., pedal rpm), is now very useful because it has been associated with user's true physiological condition (i.e., heart rate).

Thus, information provided by the pedal rpm can be effectively used to supplement information provided by heart rate. Because the bicycle's 20 control system has two sources of information about the user's exercise intensity, its performance is improved. If heart rate data is temporarily unavailable, changes in pedal rpm can be used to adjust exercise load to maintain a constant heart rate. Moreover, changes in rpm (i.e., physical or external intensity) tend to anticipate changes in heart rate (i.e., true physiological intensity). By responding to the changes in rpm, load adjustments are made more gradual and heart rate more steady.

Until the user has reached the target heart rate, the bicycle 20 seeks to continually monitor the user's heart rate. Once the user has reached the target heart rate, however, the bicycle 20 will allow (or, preferably, invite) the user to remove his hands from the sensors 38 for periods of time such as ninety seconds. When the bicycle 20 requires fresh heart rate data, it prompts the user by means of the data display 32. The user then places his hands on the sensors 38 so that the bicycle 20 can take a new sample of heart rate. If the user's heart rate is at an appropriate level, the user is again invited to remove his hands from the sensors 38. This cycle is repeated throughout the exercise.

If the system prompts the user to place his hands on the sensors 38, and the user ignores the prompt for more then forty-five seconds, a bell or beeper is activated. If the user continues to ignore the prompt for an additional fifteen seconds, the load resistance is substantially reduced. It will be observed that during periods where the user's heart rate data is unavailable, the system can use rpm data to maintain the target heart rate.

C. Hardware Description

Figure 4:
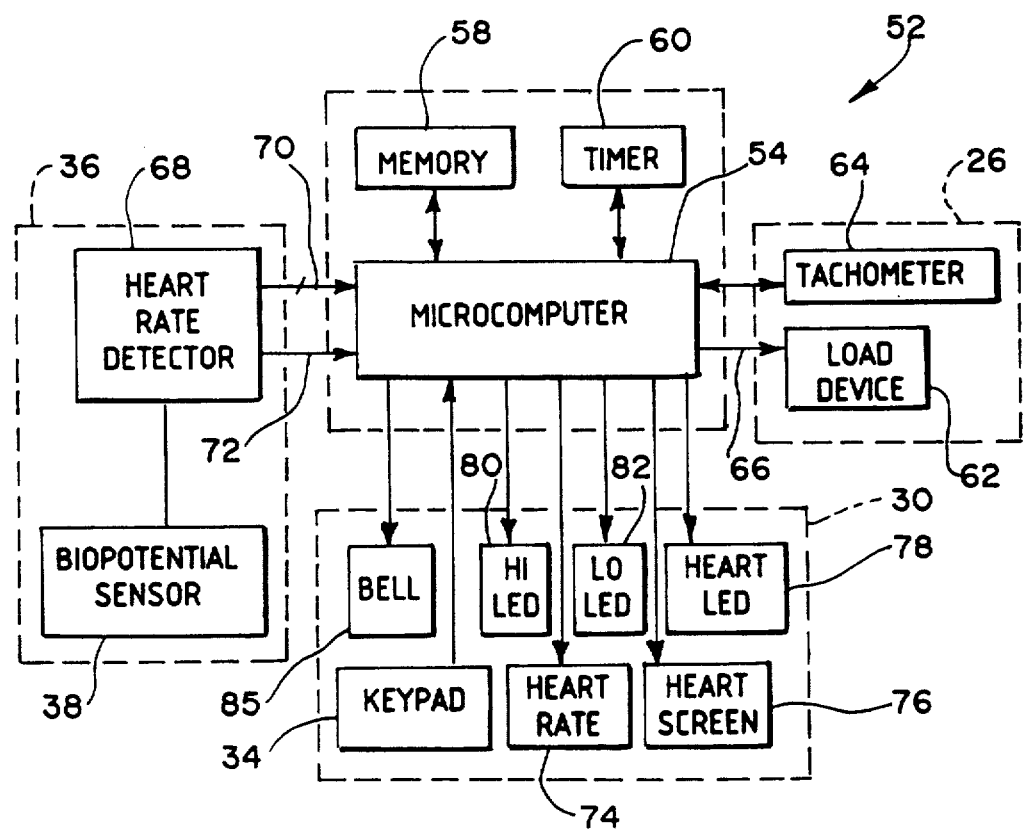
FIG. 4 is a generalized block diagram of an exercise device in accordance with the invention.

FIG. 4 is a generalized block diagram of a system 52 in accordance with the preferred embodiment of the invention which is used to implement the foregoing operations of the invention. The system 52 is illustrated herein as part of exercise bicycle 20. Of course, system 52 can be readily implemented in any of the exercise devices 20, 22 and 24, or in any other type of device providing a variable load resistance or speed control for exercise movement.

Referring to FIG. 4, the hardware elements of system 54 are illustrated. A microcomputer 54 controls system 52 and includes a memory 58 and a timer 60. In practice, the memory 58 should include both random access memory as well as read only or non-volatile memory for permanently storing the software programs which enable the microcomputer 54 to perform in accordance with the invention. The microcomputer 54 can be any suitable device such as the Motorola 68HC05. The microcomputer 54 communicates with a user via the control panel 30 (illustrated in FIG. 4 by dotted lines), which is described below in greater detail.

The microcomputer 54 controls a load device 62 mounted in the frame 26 (illustrated here by dotted lines). As described above, the load device 62 is operatively associated with the pedals 28 of the system 52 to provide a selectively variable resistance load against the exercise movement of the pedals 28 by the user. A device 64 for measuring the rate of exercise, which is preferably a tachometer, measures the rate of rotation of the pedals 28, and is accessible to the microcomputer 54 by a conventional input/output port. In some embodiments where the load device 62 is an alternator, the tachometer 64 can be implemented by simply measuring the frequency of the output of the alternator. It will be observed that the tachometer 64 measures an externally observable physical indicator of the user's exercise intensity (namely, pedal rpm).

It will be apparent to those skilled in the art of microcomputers that input/output interface circuitry may be necessary to enable communication between microcomputer 54 and external devices 62 or 64. The exact nature of this interface circuitry will vary depending on the hardware which is used to implement the invention.

Preferably, the interface between the microcomputer 54 and the load device 62 should allow the microcomputer 54 to simply write an 8 bit number of between 0 and 250 to an output port 66. The number corresponds to one of 251 evenly-spaced graduations of load level resistance covering the working range of the load device 62. In this manner, the output of the microprocessor 54 to the port 66 that is used to control the load device 62 can be viewed as a load signal. From a programming prospective, the load signal can be represented by the contents of a location in the memory 58. A driver routine is then periodically called by an interrupt to write the stored value of load resistance to the port 66.

Of course, there are innumerable ways in which a microcomputer and a load device can be interfaced, and the present invention contemplates all such alternatives to the extent that they allow the microcomputer 54 to selectively adjust the resistance level of load device 62.

The microcomputer 54 provides a convenient and practical method of implementing the invention. It will be apparent to those skilled in the art that the logical functions necessary for carrying out the invention could also be implemented using other types of digital and analog circuitry.

Figure 5:
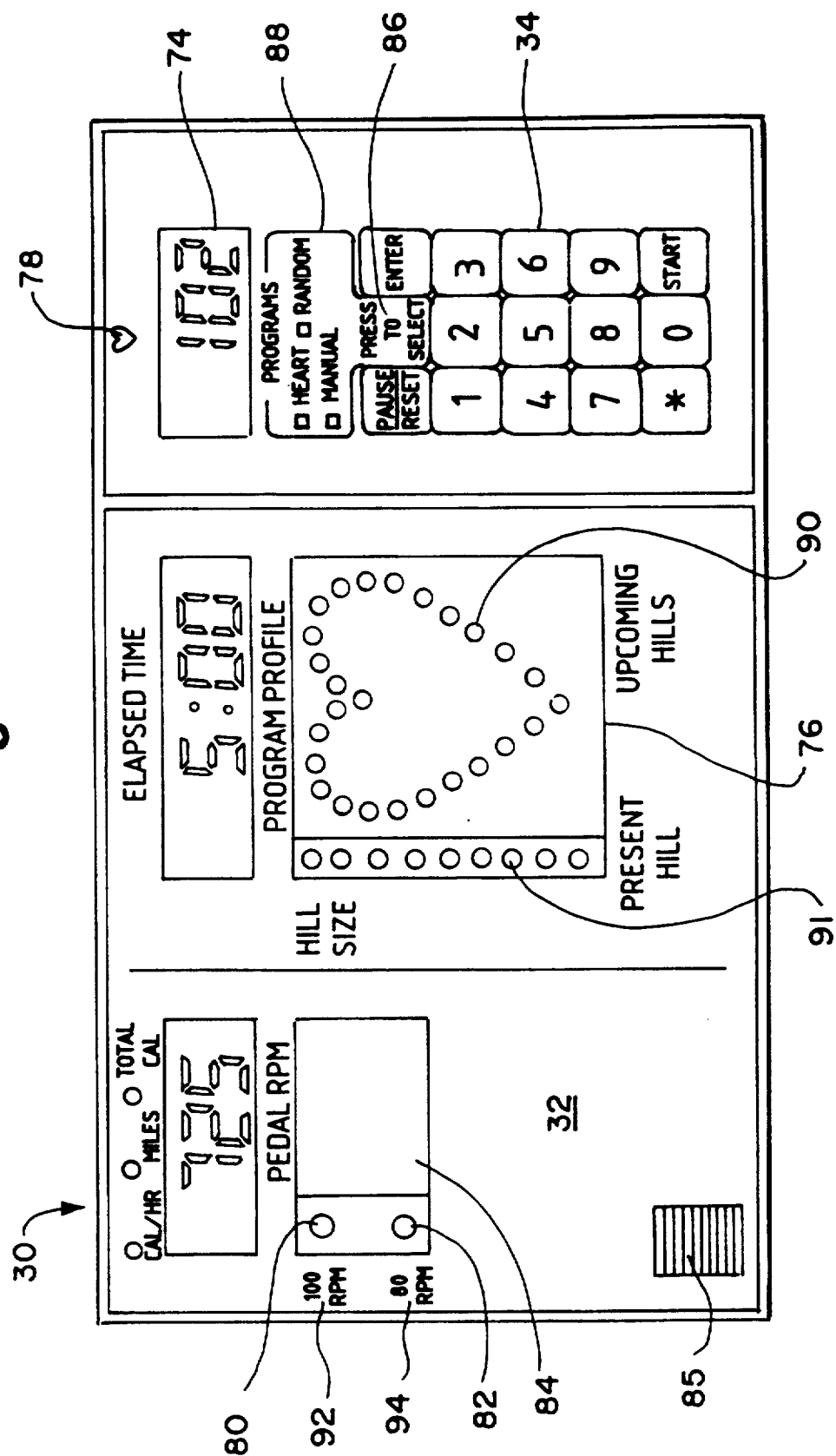
FIG. 5 is an illustration of a control and display panel in accordance with one embodiment of the invention.

The system 52 also includes the heart rate monitor 36 illustrated in FIG. 5 by a dotted line. The monitor 36 includes a pulse sensor, which may be the electrodes 38 shown in FIG. 1, and a heart rate detector 68. There are numerous commercially available systems for measuring heart rate, but as indicated above, the preferred system is disclosed in U.S. patent application Ser. No. 07/722,800, filed Jun. 28, 1991.

The heart rate detector 68 amplifies and filters the pulse signal received by the sensor 38. The pulse signal may undergo digital signal processing using circuitry within the heart rate monitor 36, or in microprocessor 54 itself. To simply this illustration, it is assumed that all processing of the pulse signal takes place within heart rate monitor 36, which in turn provides an 8 bit value of heart rate over a line 70, and a single bit (the "engagement signal") over a line 72 indicating whether the user is currently engaged with the sensor.

In some systems, the engagement signal such as described above may be unavailable. As an alternative, the system 52 can assume that the user is disengaged from the monitor (i.e., by removing his hands, removing an ear clip, or otherwise interrupting the flow of heart rate data) whenever the monitor fails to deliver a heart rate within the range of 50 to 200.

FIG. 5 is a diagram of a control panel which, for the purposes of illustration, is the control panel 30 shown in FIG. The control panel 30 interfaces with microcomputer 54 in any suitable manner such as by serial or parallel port. Because in practice the microcomputer 54 will control other functions of bicycle 20 in addition to managing heart rate, other features including an elapsed time display and a caloric consumption display are shown in FIG. 5. Contrastingly, in FIG. 4 only selected elements of the control panel 30 are illustrated.

For clarity, communication signals between microcomputer 54 and various elements of the control panel 30 are illustrated in FIG. 4 by separate arrows. In practice, suitable input/output interface circuitry can be used to facilitate communication between the microcomputer 54 and the control panel 30. As indicated, such communication might involve a serial or parallel link.

The control panel 30 includes the keypad 34, an LED heart rate display 74, an LED heart screen 76, an LED hands-on indicator 78, a high rpm LED 80, a low rpm LED 82, an LED rpm display 84, and an alarm bell 85. The specific configuration of the control panel 30, including its layout and the protocol used to communicate with the user are described in connection with the preferred embodiment of the invention as implemented in the exercise system 52. There is an infinite variety of audio and visual designs and techniques for establishing communication between the microcomputer 54 and the user, and the present invention contemplates the use of any suitable design or technique which achieves the functionality specified by the invention.

The keypad 34 is used by the user to communicate with the microcomputer 54. Conventionally, a computer controlled exercise bicycle 20 has several modes of operation. Thus, an existing program or mode of operation might allow the user to pedal at a constant level of load resistance. Another mode might enable the user to pedal at randomly selected levels of resistance. In the illustrated embodiment, the present invention is described as an additional mode of operation which can be referred to as a Heart Rate Management Mode.

The various modes of operation, including the novel Heart Rate Management Mode, may be selected by pressing a select key 86. Each time the select key 86 is pressed, one of the possible modes is selected. A panel 88 above the select key 86 displays indicia of each of the available modes. In the illustration, the available modes are depicted by the indicia "Random", "Manual" and "Heart [Rate Management]." These a modes are illustrated solely as examples. A small LED next to each indicia indicates when the mode corresponding to the indicia has been selected.

The LED heart rate display 74 displays the current measured value of the user's heart rate when the user has placed his or her hands on the sensors 38. If, for reasons explained below, the user has engaged the sensors 38 but valid heart rate data is not available, then "Hr" or other symbol is displayed in the LED heart rate display 74 to signify that no valid data is yet available.

The heart-shaped LED hands-on indicator 78 is lit by the microcomputer 54 whenever the heart rate monitor 36 signals on the line 72 that the user has engaged the sensors 38. In this case, such engagement is achieved by the user placing his or her hands on the sensors 38. For convenience, we refer to this engagement as a hands-on condition, although it to be understood that other types of engagement (such as by ear clip) are contemplated by the invention.

If the heart monitor 36 signals that the user's hands have engaged sensors 38, microcomputer 54 enables the heart-shaped LED hands-on indicator 78. Generally, the heart-shaped LED hands-on indicator 78 is lit concurrently with the display of heart rate data (or the "Hr" symbol, as the case may be) in the LED heart rate display 74.

The LED heart screen 76 is preferably an array of LEDs on which a heart 90 or other suitable symbol can be displayed. A row 91 of LED's can be used as a meter to display the relative value of load resistance. As will be explained, the heart symbol 90 is displayed by microcomputer 54 during those times when the user has his or her hands on the sensors 38. When the heart symbol is not displayed, the user is free to remove his hands from the sensors 38. If the microcomputer 54 determines that the user's current heart rate data is required, and the user's hands are not on the sensors, then the microcomputer 54 can flash the heart symbol to advise the user to place his or her hands on the sensors 38.

The LED rpm display 84 displays the current rpm or other measure of the rate of exercise movement performed by the user. The high rpm LED 80 and low rpm LED 82 are used to prompt the user to pedal at predetermined high and low rpm levels, respectively. Indicia 92 and 94 next to the high and low rpm LEDs 80 and 82, respectively, indicate that the predetermined high and low rpm levels are 100 and 80 rpm, respectively.

D. Software Description

1. Main Routine

Figure 6:
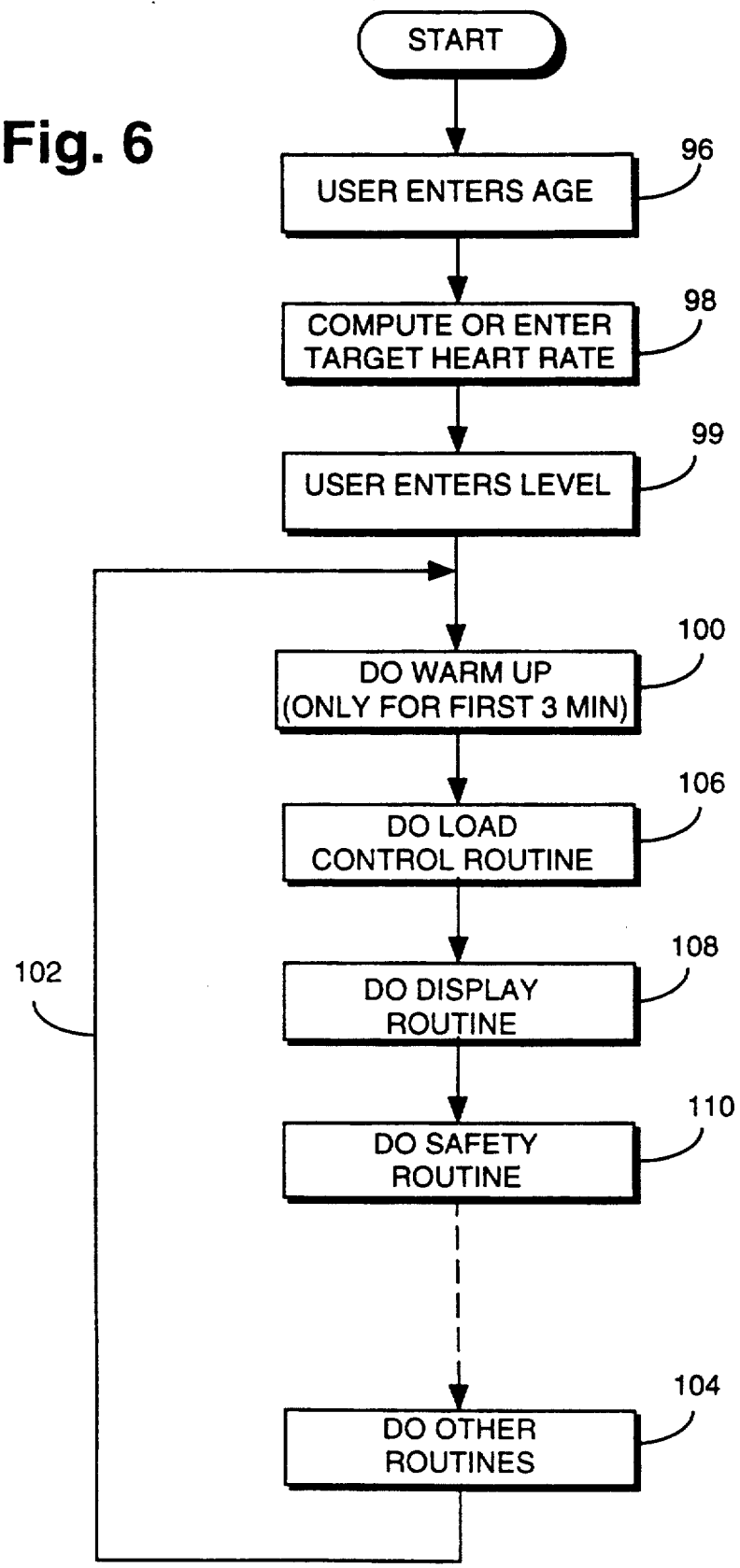
FIGS. 6 through 15 are logic flow charts of the software program operating in the memory of the microcomputer shown in FIG. 4 which performs the functions specified by the invention.

The software routines which enable the foregoing operation of the invention are resident in the memory 58 of microcomputer 54. Referring to FIGS. 6-15, logic flow charts of the software resident in memory 58 are provided. For convenience, selected variable names used in FIGS. 6-15 are included in parentheses throughout this specification. The main routine which calls the other major software modules is illustrated in FIG. 6. Beginning at a block 96, the microcomputer 54 prompts the user to enter his age (AGE). The microprocessor may use the LED heart rate display 74 for prompting, and the user may use the keypad 34 for data entry.

At a block 98, microcomputer 54 computes a target heart rate in accordance with a predetermined formula. A embodiment, the target heart rate (HR_TGT) is set to:

$$HR\_TGT = 220 - AGE*0.7$$

Alternatively, the user may enter a target heart rate of his or her own selection.

At a block 99 the user enters a desired initial exercise load resistance level (LEVEL). Typically the range of possible exercise levels is scaled from 0 to 12.

At a block 100, the microcomputer enters a main driver loop 102 in which the major software modules implementing the invention in the system 52 are called. It will be noted that the software resident in the memory 58 may include other functions not related to the invention. These functions may be executed in the main driver loop 102, as indicated by a block 104.

At the block 100, the user is prompted to ride the bicycle 20 for a predetermined warm up period such as three minutes during which time the load level will be established and maintained the constant value LEVEL which the user selected at the block 99. After completion of the three minute warm-up, the warm-up routine 100 is suppressed and is no longer called during each iteration of main driver loop 102.

As discussed in more detail below, the major software elements implementing the invention are the load control module shown in a block 106, the display module shown in a block 108, and the safety module shown in block 110. Depending on the execution speed of the microcomputer 54, a number of iterations of main driver loop 102 will be completed each second. In practice, it is desirable to execute the load control module 106 about once each second. The display and safety modules 108 and 110 may be executed more frequently. An interrupt is triggered once per second and sets a flag (not shown). The load control module 106 is called from the main driver loop 102 only when this flag is set. It will be noted that during the three-minute warm-up, the load control routine is suppressed and is not called with each iteration of the main driver loop 102.

2. Load Control Module

Figure 7:
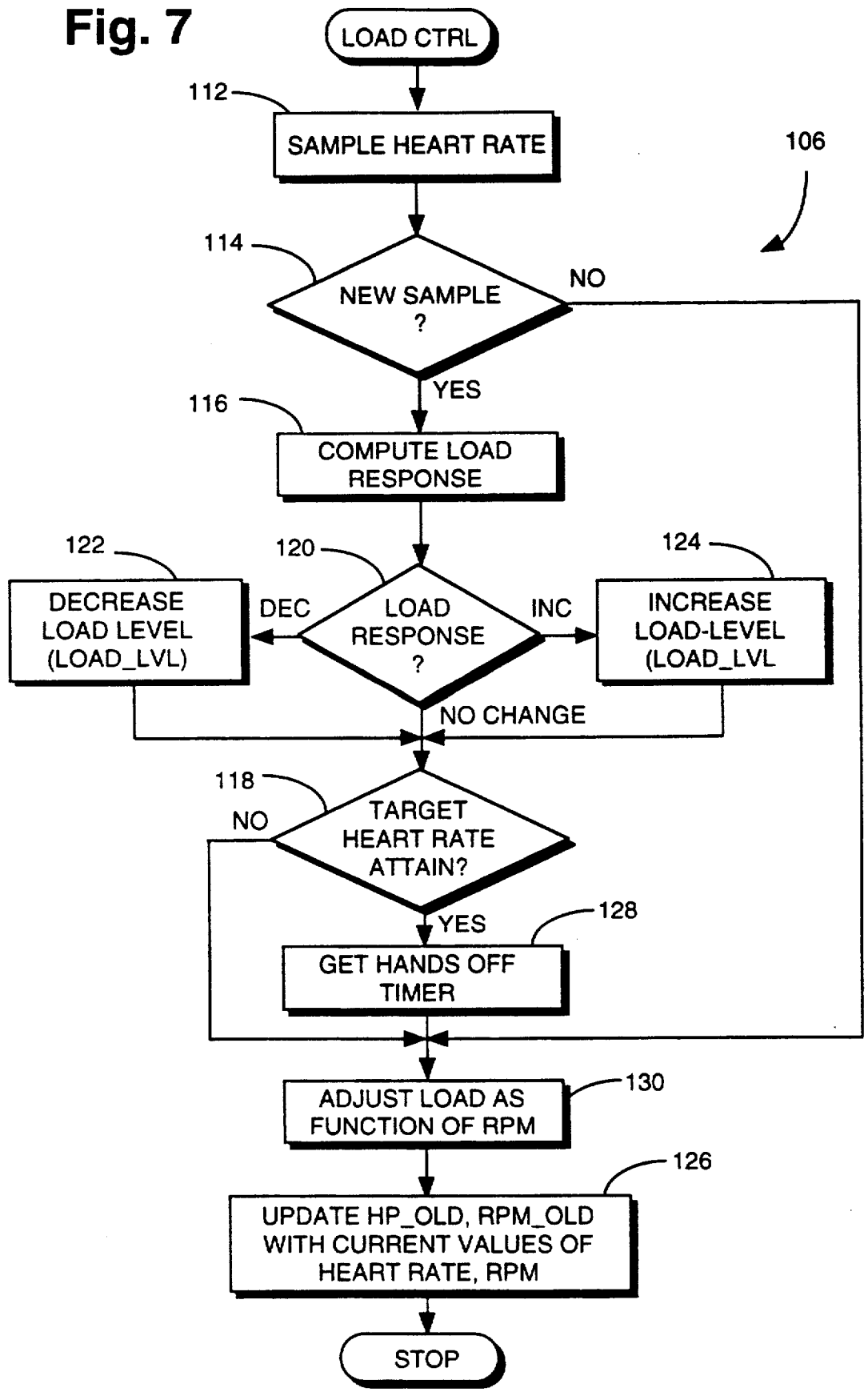

FIG. 7 is a logic flow chart of the load control module 106. At a block 112, microcomputer 54 interrogates heart rate monitor 36 to determine if a current sample of the user's heart rate is available. If such a sample is available, it is stored in a variable HR_NEW.

At a decisional block 114, if a new sample was acquired at block 112, then control continues to a block 116, where the change in load resistance (the "load response") is computed on the basis of the freshly sampled heart rate and other variables as discussed below. Otherwise control skips the block 116 and jumps to a block 130, discussed below. After execution of the block 116, control branches at a decisional block 120 depending on whether the load response is positive or negative. If load response is negative, then the microcomputer 54 decreases load resistance by calling a decrease load routine shown in a block 122. If load response is positive, then the microcomputer 54 increases load resistance by calling an increase load routine shown in a block 124.

After load resistance is adjusted, control moves to a block 118, where microcomputer 54 determines whether the user has attained the target heart rate (the "target heart rate condition"). Preferably, a boolean flag (TARGET) indicates whether the target heart rate condition exists or has existed. The TARGET flag is set at the block 112 as soon as the user's current heart rate is greater than or equal to the target heart rate. Once the target heart rate condition is achieved, the TARGET flag remains set for the duration of the exercise, even if the user's actual heart rate subsequently falls below the target heart rate.

If the user has not yet reached the target heart rate condition, then control skips to the block 130, discussed below. If the user, however, has attained the target heart rate, then the microcomputer 54 calls a set-hands-off-timer routine shown at block 128 and discussed below in greater detail. The hands-off-timer routine examines the change in the user's heart rate over time, and on the basis of that examination, sets a time period during which the user is free to remove his hands from sensors 38.

After the hands-off timer is set, microcomputer 54 adjusts load resistance as a function of the change in the user's rpm, as illustrated by the block 130. As discussed above, the idea behind adjusting load resistance as a function of RPM is to take advantage of the information about the user's exercise intensity that can be gleaned from rpm.

As the user pedals faster or slower at a particular level of load resistance, the user's heart rate will fluctuate. The change in the rate of rate of exercise is an externally observable physical indicator of exercise intensity, and is in fact a predictive measure of future changes in the user's true physiological exercise intensity, as measured by heart rate, for example. By increasing the load when rpm decreases (and, conversely, decreasing the load when the rpm increases), microcomputer 54 can reduce fluctuations in user heart rate which would otherwise result from the change in pedal rpm.

By using rpm as an indicator of exercise intensity, system 52 can maintain the user's heart rate even when heart rate data is unavailable, such as when the hands-off timer is set. This enables the system 52 to set the hands-off timer (discussed above) for relatively long periods such as ninety seconds. Moreover, the user is free to change the rate of pedaling to make exercise more interesting.

After setting the hands-off timer and adjusting load resistance as a function of rpm, the microcomputer 54 performs housekeeping functions illustrated by the block 126. Specifically, the current values of rpm and heart rate (RPM_NEW and HR_NEW) are preserved in memory (in RPM_OLD and HR_OLD, respectively) so that the changes in rpm and heart rate may be determined during the next iteration of the load control module 106.

Figure 8:
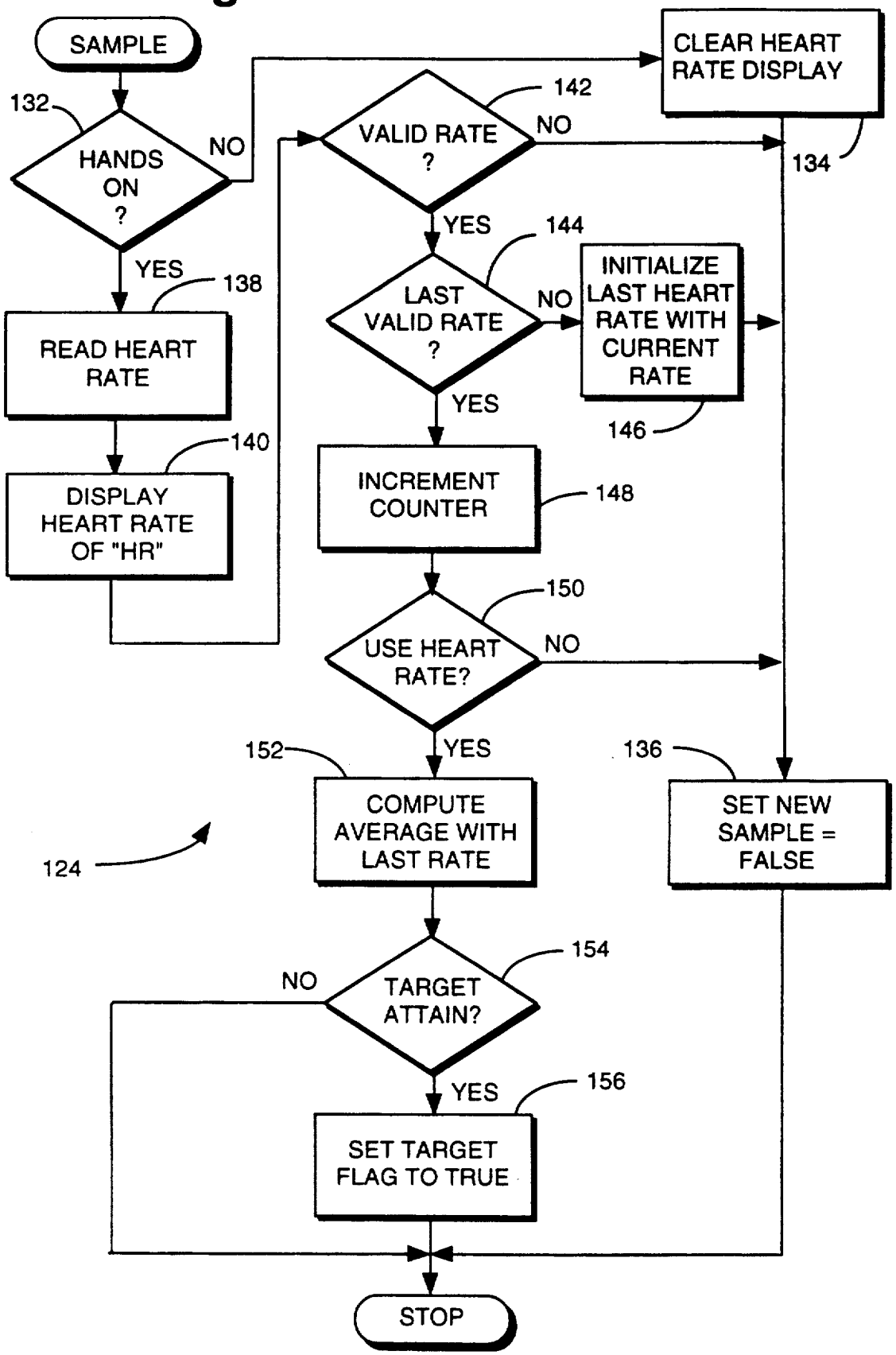

The functions of the load control module 106 discussed above are now considered in greater detail Referring to FIG. 8, the sample-heart-rate routine 112 is more fully described. In accordance with this routine, the microcomputer 54 periodically samples the output of the heart rate monitor 36. It will be noted that the specific techniques disclosed in connection with sample routine 112 have been found to work well, but represent just one of many alternatives which will be readily apparent to those skilled in the art.

Beginning at a block 132, the condition of the engagement signal or "hands-on" bit (provided by the heart rate monitor 36 at the line 72) is determined. If the user is not engaging the sensors 36, it means that no current heart rate data is available. As shown at a block 134, the microcomputer 54 clears the LED heart rate display 74 and disables the LED hands-on indicator 78 of the control panel 30 (as shown in FIG. 5). The microcomputer 54 then sets the new-sample flag (used in connection with the block 114 discussed above) to false, as shown in a block 136.

If, however, the user is engaging the pulse sensors 38 (the "hands-on condition"), then the microcomputer 54 reads the user's heart rate (provided by the heart rate monitor 36 at the line 70), as shown at a block 138. This heart rate is then stored in a memory variable (HR_NEW) and displayed on the LED heart rate display 74. The LED hands-on indicator 78 is also enabled. Thus, each time the user places his hands on the pulse sensors 38, his heart rate is displayed on control panel 30.

If, as may be the case initially, the user's hands are on the pulse sensors 38 but heart rate monitor 36 has not yet generated a valid heart rate reading (i.e., a value of between 50 and 200 beats per minute), then the microcomputer 54 generates an "Hr" or other suitable symbol in the LED heart rate display 74.

At a decisional block 142, if the newly sampled heart rate is not valid, then microcomputer 54 skips to the block 136 where the new sample flag is set to false. As discussed below, the heart rate value used to adjust load is preferably an average of the current and last measured heart rates (HR_NEW, HR_OLD). Thus, if the current heart rates sample is valid, the microcomputer 54 proceeds to a decisional block 144 where it examines the last measured heart rate (HR_OLD) stored in the memory 58. If the last measured heart rate is invalid, the microcomputer 54 skips to a block 146, where the value of HR_OLD is updated with the value of HR_NEW. Control then moves to the block 136, where the new sample flag is set to false.

If the last measured heart rate is valid, the microcomputer 54 continues to a block 148, where it increments a counter. The function of the counter is to track iterations of the sample heart rate routine 112. Depending on the performance of heart rate monitor 36, it may be desirable to use every other heart rate sample. In this case, if the value of the counter is an even number, then at a block 150 the microcomputer 54 uses the currently measured heart rate to compute an average heart rate, as illustrated at a block 152. Otherwise, the currently measured sample is discarded, and control skips to the block 136, where the new sample flag is set to false.

Another use of the counter is to suppress the very first sample of heart rate data after the user has placed his hands on the sensors 38. This can be accomplished by setting the counter to −1 at the block 146. In this manner, once heart rate monitor 36 begins delivering valid heart rate data to the microcomputer 54, the first valid sample (corresponding to a counter value of −1) is discarded.

The average heart rate computed at the block 152 is computed by taking the average of the old and current heart rate values (i.e., (HR_OLD plus HR_NEW)/2), and storing the result as the current heart rate. By computing this running average, minor aberrations and fluctuations in heart rate data are filtered to improve system stability.

The microcomputer then compares the average computed heart rate (HR_NEW) to the target heart rate (HR_TGT) stored in the memory 58, as shown at a block 154. If the average computed heart rate (HR_NEW) is greater than or equal to the target heart rate, a flag (TARGET) is set true, as illustrated in a block 156. The TARGET flag remains true for the duration of the exercise period, and indicates that the user has reached target heart rate condition.

Upon completion of the blocks 156 or 136, as the case may be, the sample-heart-rate routine 124 is terminated, and control returns to the load control module 106 illustrated in FIG. 7. As discussed above, if the sample-heart-rate-routine has successfully acquired a sample heart rate, the new sample flag will be set to true, and, as illustrated in the block 114 of FIG. 7, the microcomputer 54 will proceed to compute a change in the load signal or "load response", as illustrated in the block 116.

Figure 9:
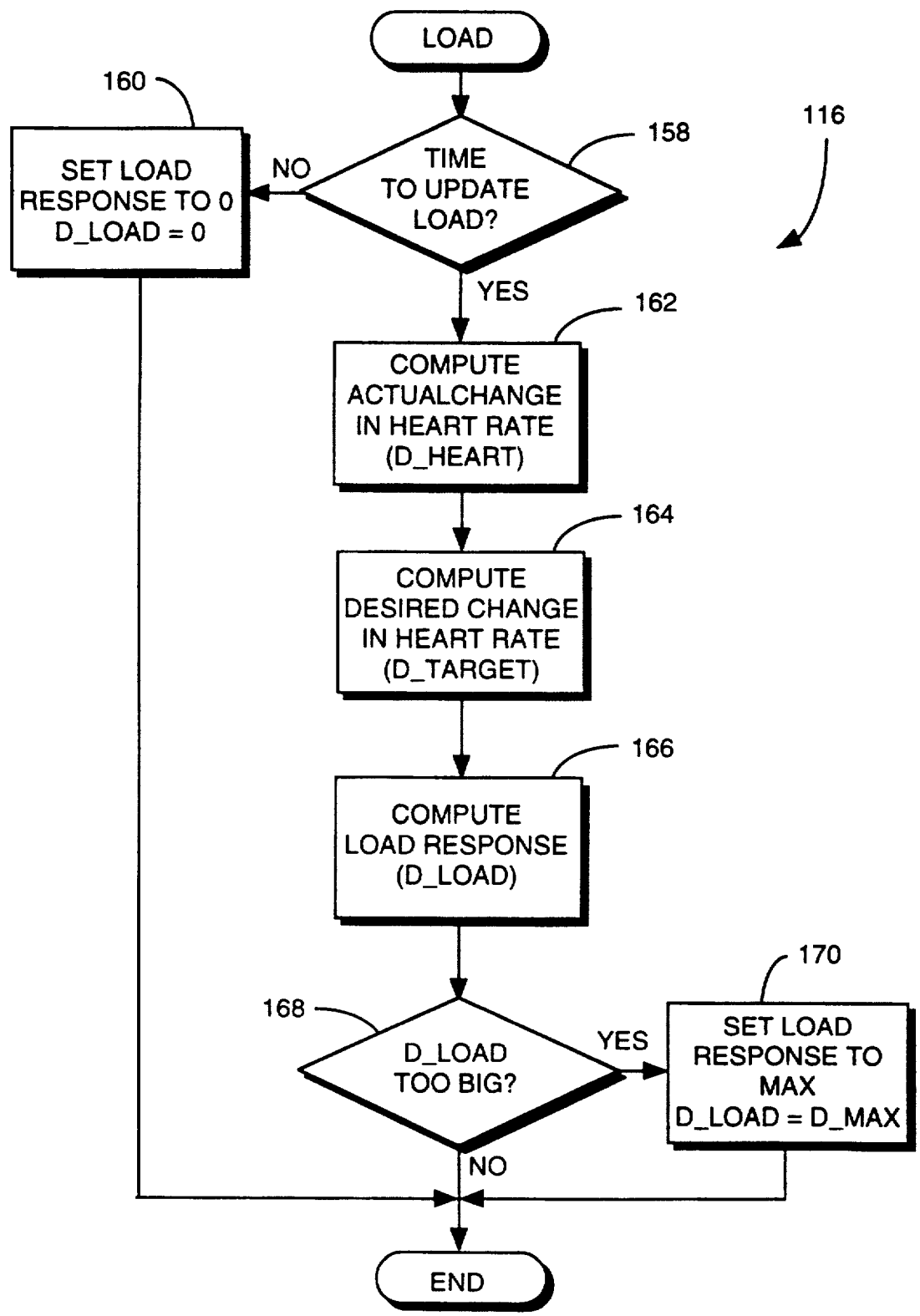

Referring to FIG. 9, the operation of the load response routine 116 is illustrated in greater detail. The function of the load response routine 116 is to determine a load response, i.e. the amount by which microprocessor 54 *changes* the value of the load signal 66 to maintain or attain the target heart rate.

The microprocessor 54 first determines at a block 158 whether it is time to update the load signal. While load response can be updated with each iteration of the load response routine, it may be preferably to update less frequently to avoid excessive changes in load resistance.

To this end, load response can be updated on each $n^{th}$ iteration, where n is a number such as 6. This can be determined by examining the incremented value of the counter (HR_CTR) at the block 148 to determine if the counter's current value is a whole number multiple of n.

If it is not time to update the load signal 66, the microcomputer 54 sets the load response variable (D_LOAD) to zero, as illustrated at a block 160, and terminates the load response routine 116. If it is time to update the load signal 66, then microcomputer 54 calculates the load response (D_LOAD) as illustrated by blocks 162 through 170 of FIG. 9. First, the actual change (D_HEART) in the user's heart rate is computed by subtracting the current heart rate value (HR_NEW) from the old heart rate value (HR_OLD). Next, the desired change in heart rate (D_TARGET) is computed by subtracting the target heart rate value (HR_TGT) from the current heart rate value (HR_NEW). Finally, the load response (D_LOAD) is calculated as the difference between the desired change (D_TARGET) in heart rate minus the actual change (D_HEART)in heart rate multiplied by a scaling constant ($K_1$) (i.e., (D_TARGET−D_HEART)*$K_1$)

The scaling constant $K_1$ is determined by empirical calibration of the particular device in which the invention is implemented, and simply serves to convert the calculated difference between D_TARGET and D_HEART into units of load resistance. In some cases, performance may be improved by weighting D_TARGET relative to D_HEART.

It will be noted that the foregoing technique computes load response as function of the differential in heart rate. Other techniques for calculating load response as a function of heart rate are known, and the foregoing is offered as one which we have found particularly effective. However, the invention contemplates the use of any suitable technique. In accordance with one alternative, for example, the load response could be computed (albeit less effectively) as a function of the difference between actual and target heart rate.

As a precaution, the calculated load response is compared to a predetermined maximum (D_MAX), as shown in a block 168. If the load response (D_LOAD) exceeds the predetermined maximum, then load response is set to the predetermined maximum. It will be noted that load response represents the change in load, as opposed to the total magnitude of load. Thus, the predetermined maximum (D_MAX) does not represent the maximum load to which a user may be subjected, but rather the maximum increase which may be imposed during one iteration of the load control module 106. This prevents load from increasing at an excessive rate which might otherwise prematurely exhaust the user.

Referring back to FIG. 7, after load response (D_LOAD) is computed at the block 116, control branches at the decisional block 120 depending on whether load response is positive, negative or zero. If the load response is negative, then the load signal is adjusted to decrease total load resistance, as shown in the block 122. If the load response is positive, then the load signal is adjusted to increase the total load resistance, as shown in the block 124. If the load response is zero, no change in load resistance is required, and control continues to the block 118.

Figures 10, 12:
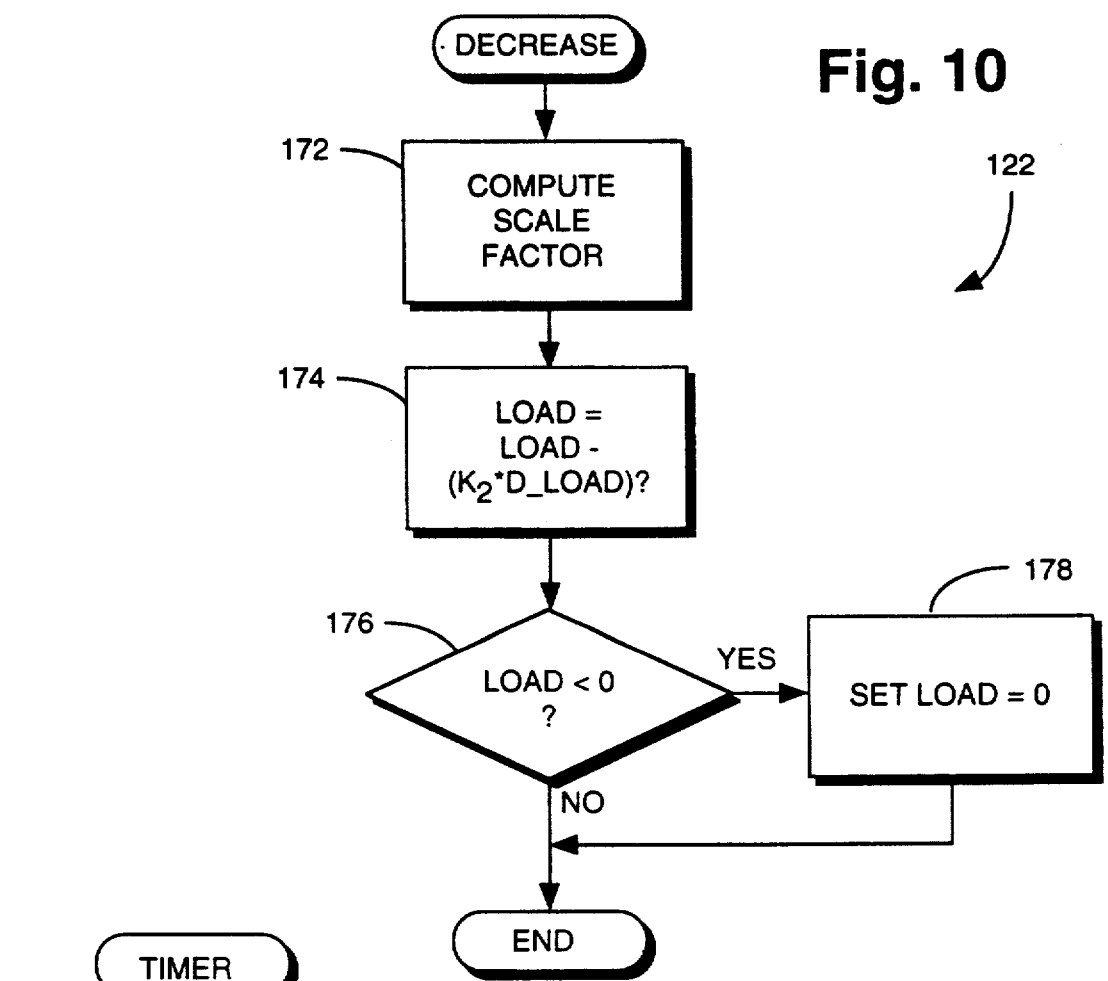

Referring to FIG. 10, the decrease load routine shown at the block 122 of FIG. 7 is illustrated in greater detail. Before adjusting the load signal, microcomputer 54 calculates a scaling factor $K_2$, which may simply be a constant such as 1.25. The scaling factor $K_2$ is determined by empirical calibration of the particular device in which the invention is implemented, and simply serves to convert the calculated load response (D_LOAD) into the desired units of load resistance.

Scaling factor $K_2$ may also be a function of the user-entered load level (LEVEL). It is the case that users who enter high initial load levels typically require more dramatic adjustments to level so as not to overshoot the target heart rate. To compensate for this phenomenon, the scaling factor $K_2$ may be computed in accordance with the following formula:

$$K_2 = 1.25 + LEVEL/6.9$$

In practice, specific embodiments should be calibrated, and empirically determined values may be used in lieu of 1.25 and 6.9 above.

After the scaling factor $K_2$ is calculated, the load signal is adjusted as shown by block 174 of FIG. 10. Specifically, the value of load in memory 58 (LOAD) is arithmetically decreased by a value equal to the scaling factor multiplied by the load response (LOAD=LOAD−($K_2$*D_LOAD)). If the resulting value of load resistance is less than zero, then load resistance is set equal to zero, as shown in blocks 176 and 178.

Figure 11:
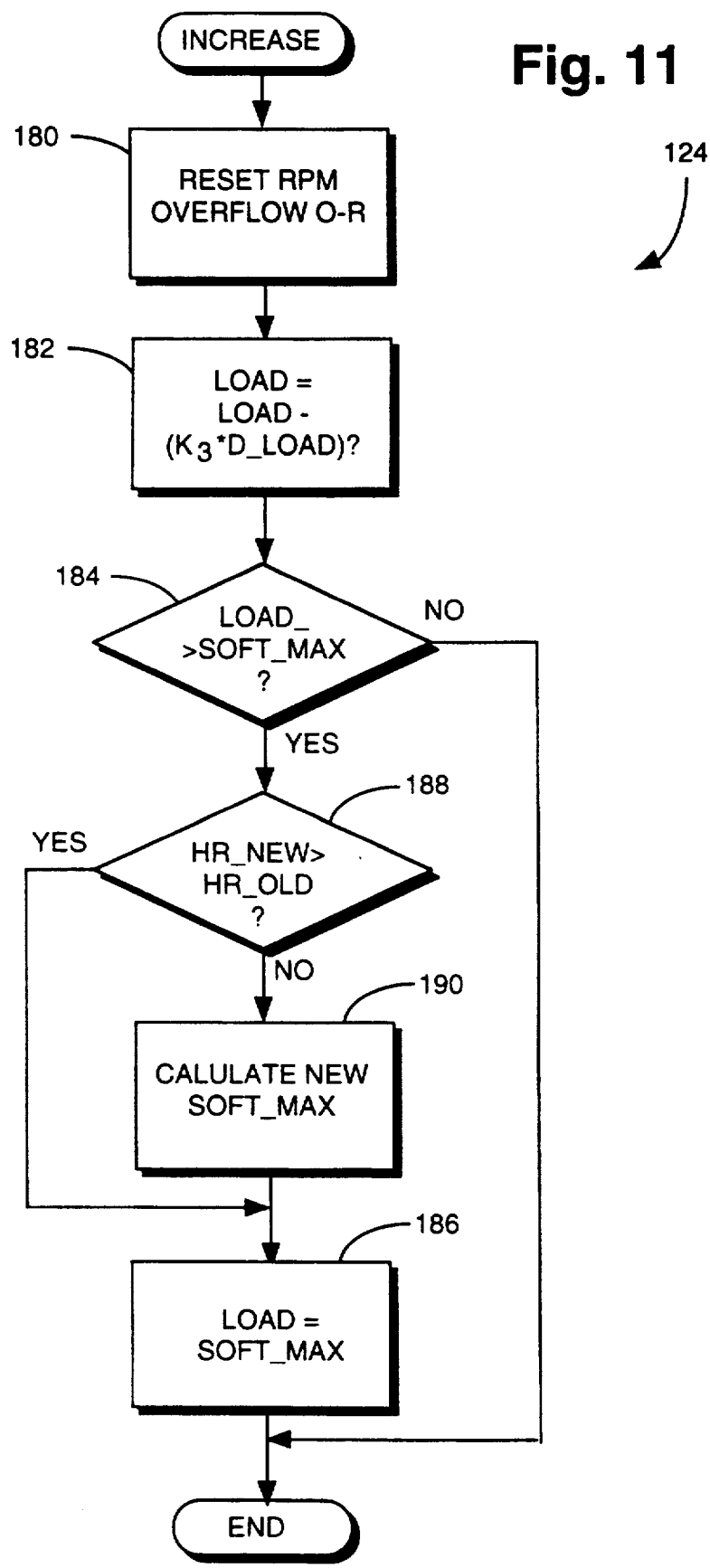

Referring to FIG. 11, the increase load routine shown at the block 124 of FIG. 7 is illustrated in greater detail. Before adjusting the load signal, microcomputer 54 calculates a scaling factor $K_3$. The scaling factor $K_3$ is determined by empirical calibration of the particular device in which the invention is implemented, and simply serves to convert the calculated load response (D_LOAD) into the desired units of load resistance. Scaling factor $K_3$ may also be set to arbitrarily reduce the load increase. For example, even if the load response does not require scaling, it may be desirable for safety and comfort considerations to use a value of 0.75 for $K_3$ to reduce the increase load response.

Microcomputer 54 may also reset an rpm overflow counter (RPM_CTR), as shown in a block 180. The function of the rpm overflow counter is discussed below in more detail.

After the scaling factor $K_3$ is calculated, the load signal is adjusted as shown by block 182 of FIG. 11. Specifically, the value of load resistance in memory 58 (LOAD) is arithmetically increased by a value equal to the scaling factor $K_3$ multiplied by the load response (LOAD=LOAD+($K_3$*D_LOAD)). If the resulting value of load resistance (LOAD) does not exceed a predetermined soft maximum value (SOFT_MAX), then the increase load routine 124 terminates.

If the resulting value of load resistance (LOAD) does exceed the soft maximum (SOFT_MAX), then load resistance may be set equal to the soft maximum, as shown in a block 186. The soft maximum is preferably calculated at the beginning of exercise as a function of the user-selected exercise level (LEVEL), which is entered at block 98 of FIG. 6. It will be noted that the difficulty of exercise level (LEVEL) selected by the user is typically indicative of the user's overall fitness level (or at least the user's perceived fitness). Thus, the value of the soft maximum can be higher where the user's has selected a more difficult initial exercise level (LEVEL).

For example, if the load resistance has a range of 0 through 250 (corresponding to possible numerical values of the load signal), and the user selects an initial load level (LEVEL) of 6 (out of 12), then the user-selected load level could be said to correspond to a load signal of 125 (about one-half of 250). Preferably, the soft maximum (SOFT_MAX) would be set to 127.

As illustrated at a block 188 of FIG. 11, it is possible that a user's heart rate is decreasing (i.e., HR_NEW<HR_OLD) even though load resistance has reached the soft maximum. In this case, it is desirable to gradually increase the soft maximum, as shown by a block 190. Thus, at each iteration of the block 190, the value of the soft maximum is incremented, such as by one, until the value of the soft maximum reaches a predetermined hard maximum (HARD_MAX).

The value of the hard maximum is determined in accordance with the following formula:

$$HARD\_MAX = SOFT\_MAX + (0.25*(MAX - SOFT\_MAX)),$$

where SOFT_MAX is equal to the initial value of the soft maximum (i.e., user-selected level), and MAX is equal to largest value of load resistance which load device 62 can impose on the user.

By adjusting load resistance in accordance with the user's heart rate, such as described above, the system 52 will tend to establish and maintain the user's heart rate at or near the target heart rate. Preferably, during steady state exercise, the user's heart rate should be within 5 beats per minute of the target heart rate. We have found that even better results have been obtainable with devices built in accordance with this invention.

Referring back to FIG. 7, after the load signal has been adjusted at blocks 122 and 124, as the case may be, the microcomputer 54 determines whether a target heart rate condition exists, as shown by block 118. Before a user reaches his target heart rate, it is necessary to closely monitor the user's heart rate so that the appropriate load value can be selected. Once the user reaches his target heart rate, it is no longer necessary to continually monitor heart rate. This is significant because the user may wish to remove his hands from sensors 38.

Thus, if the user has reached a target heart rate, the microcomputer 54 will determine if it is possible for the user to remove his hands from the pulse sensors 38, and if so, for how long. This determination is performed by the set-hands-off-timer routine shown at the block 128. The details of the set-hands-off-timer routine are illustrated in FIG. 12. The microcomputer 54 calculates the difference between the actual and desired rates of change in heart rate (D_TARGET−D_HEART), as shown in block 192. If the absolute value of the difference is below a predetermined threshold (preferably 8), then control continues to a block 194. Otherwise, the routine terminates. At the block 194, a time limit is selected in accordance with the following hands-off time limit table:

| Time Limit (sec) | Difference |
|---|---|
| 15 | 6–7 |
| 30 | 4–5 |
| 60 | 2–3 |
| 90 | 0–1 |

Preferably, the time limit is set to 15 seconds for the first iteration of the block 194 regardless of the actual difference between D_HEART and D_TARGET.

The selected time limit is used to set the a hands-off timer, which may be a memory location that is periodically decremented by an interrupt generated by the timer 60. Thus, the contents of the hands-off timer (HR_TMR) at any given moment represent the period of time in seconds remaining in which the user need not engage pulse sensors 38. The value contained in the hands-off timer is automatically decremented by one each second. Preferably, the hands-off timer is reset to zero if microcomputer 54 detects a hand-on condition at the block 132.

It is understood that the present invention is by no means limited to heart rate detectors in which the user places his hands on electrodes. The foregoing routines are readily adaptable to any type of system wherein the user somehow engages a pulse sensor. For example, in a conventional ear-clip type detector, the hands-on signal described above would be replaced by a signal indicating whether the detector was engaged with the user's ear. When the hands-off timer has a positive value, the user would be permitted to remove the ear clip.

Referring back to FIG. 7, after the hands-off timer has been set, the microcomputer 54 proceeds to block 130, where the load resistance is adjusted as a function changes in pedal rpm or other measure of the rate of exercise. It will be noted that pedal rpm is an externally observable physical indicator of the user's exercise intensity (as opposed to a physiological indicator such as heart rate). It will be noted that the rpm-based adjustment at block 130 takes place even if no new heart rate data is available (i.e., the new sample condition is false). In this manner, the invention provides for heart rate maintenance even during times when heart rate data is not available.

Figure 13:
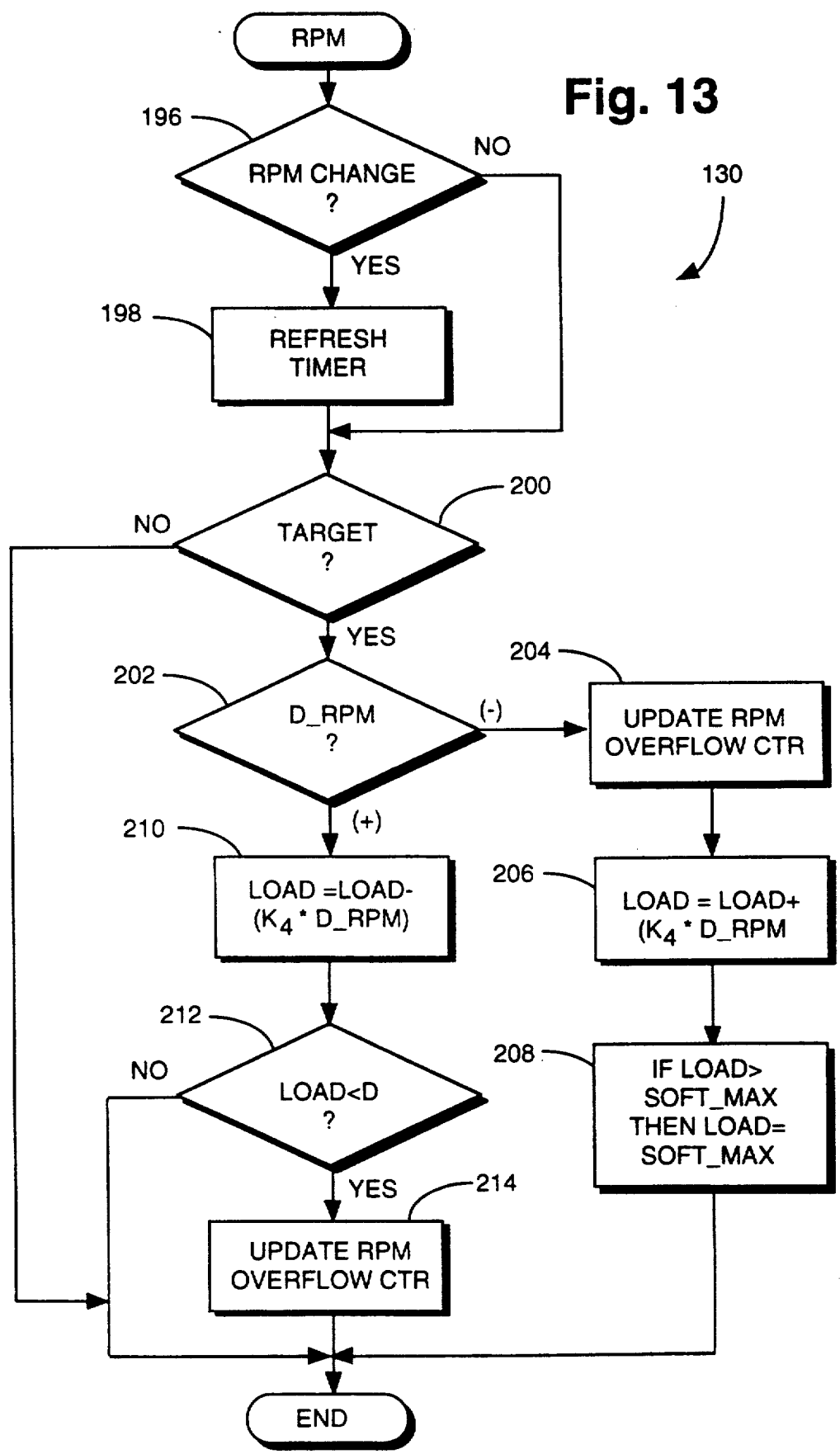

The operation of the rpm-based adjustment routine 130 is illustrated in greater detail by FIG. 13. As shown in blocks 196 and 198, microcomputer 54 initially reads the current value of rpm from tachometer 64. The current value (RPM_NEW) is compared to the last value (RPM_OLD). If the change in rpm (D_RPM=RPM_NEW−RPM_OLD) is greater than a predetermined threshold (such as 6 rpm), then the hands-off timer is reset to the minimum time period (in this case, 15 seconds) set forth in the hands off time limit table discussed above, unless the hands-off timer already has a value below that minimum time. The rationale behind resetting the hands-off timer is that great fluctuations in pedal rpm are likely to be accompanied by great fluctuations in heart rate, and, therefore, additional heart rate data is required.

The microcomputer 54 then determines whether a target heart rate condition has been attained, as shown in the block 200. If the condition has not been attained, the rpm-based adjustment routine 130 terminates without further action. No rpm-based adjustment is required in this case because until the target heart rate has been obtained, the user maintains his hands on the sensors 38, providing a steady stream of heart rate data which can be used by the load response routine 116 to control heart rate.

As shown at blocks 202–206, if rpm is decreasing (D_RPM<0), then the load resistance is adjusted upward by arithmetically adding the change in rpm (multiplied by a scaling constant, $K_4$, if necessary) to the value of load resistance stored in memory. Thus, $$LOAD = LOAD + (K_4 * D_{13}RPM)$$

It will be noted that before the change in rpm is added to the value of load, it is first subtracted from the value of the rpm overflow counter (RPM_CTR), as shown in the block 204. The rpm overflow counter is explained below in detail.

At the block 204, the rpm overflow counter is reduced to a value no lower than zero by the amount of the change in rpm (D_RPM). If the change in rpm is greater than or equal to the value of the rpm overflow counter, then the change in rpm is reduced by the value of the rpm overflow counter, $$D\_RPM - RPM\_CTR$$

and the rpm overflow counter is set to zero. Otherwise, the value of the rpm counter is reduced by the change in rpm, $$RPM\_CTR = RPM\_CTR - D\_RPM,$$

and the change in rpm is set to zero.

After the value of load resistance has been adjusted by the change in rpm, the resulting value of load resistance (LOAD) is compared to the current value of the maximum (SOFT_MAX), as shown in a block 208. If the resulting value of load resistance exceeds the soft maximum, then load resistance is set equal to the soft maximum.

Alternatively, if at the block 202 rpm is increasing, then control continues to a block 210 where the load resistance is adjusted downward by arithmetically subtracting the change in rpm (multiplied by a scaling constant, $K_5$, if necessary) to the value of load resistance stored in memory. Thus, $$LOAD = LOAD - (K_5 * D\_RPM)$$

As shown in blocks 210 and 214, if the resulting value of load resistance is less then zero (i.e., LOAD < 0), then the load resistance is set to zero, and the rpm overflow counter is incremented by the amount by which the term $K_5 * D\_RPM$ exceeds the initial value of load.

It will be observed that, because load resistance may not take a negative value, the rpm overflow counter preserves the amount by which load resistance would otherwise be negative. As discussed above, when microcomputer 54 adds to load resistance on the basis of decreasing rpm (such as at the blocks 204-206), it first attempts to deplete the overflow represented by the rpm overflow counter, as discussed above. For example, suppose a user accelerates pedaling (i.e., increases rpm) over a period of time, and, at some point during this acceleration, load resistance is driven to zero by repeated iterations of the blocks 210 and 214. Because the rpm overflow counter will contain a nonzero value, the load resistance will not immediately be increased when the user's acceleration peaks and begins to decline. Rather, the load resistance will remain at zero, while the rpm overflow counter absorbs the changes in rpm. When the value of the rpm overflow counter is reduced to zero, successive reductions in pedal rpm will begin to result in higher load resistance.

3. Display Module

Figure 14:
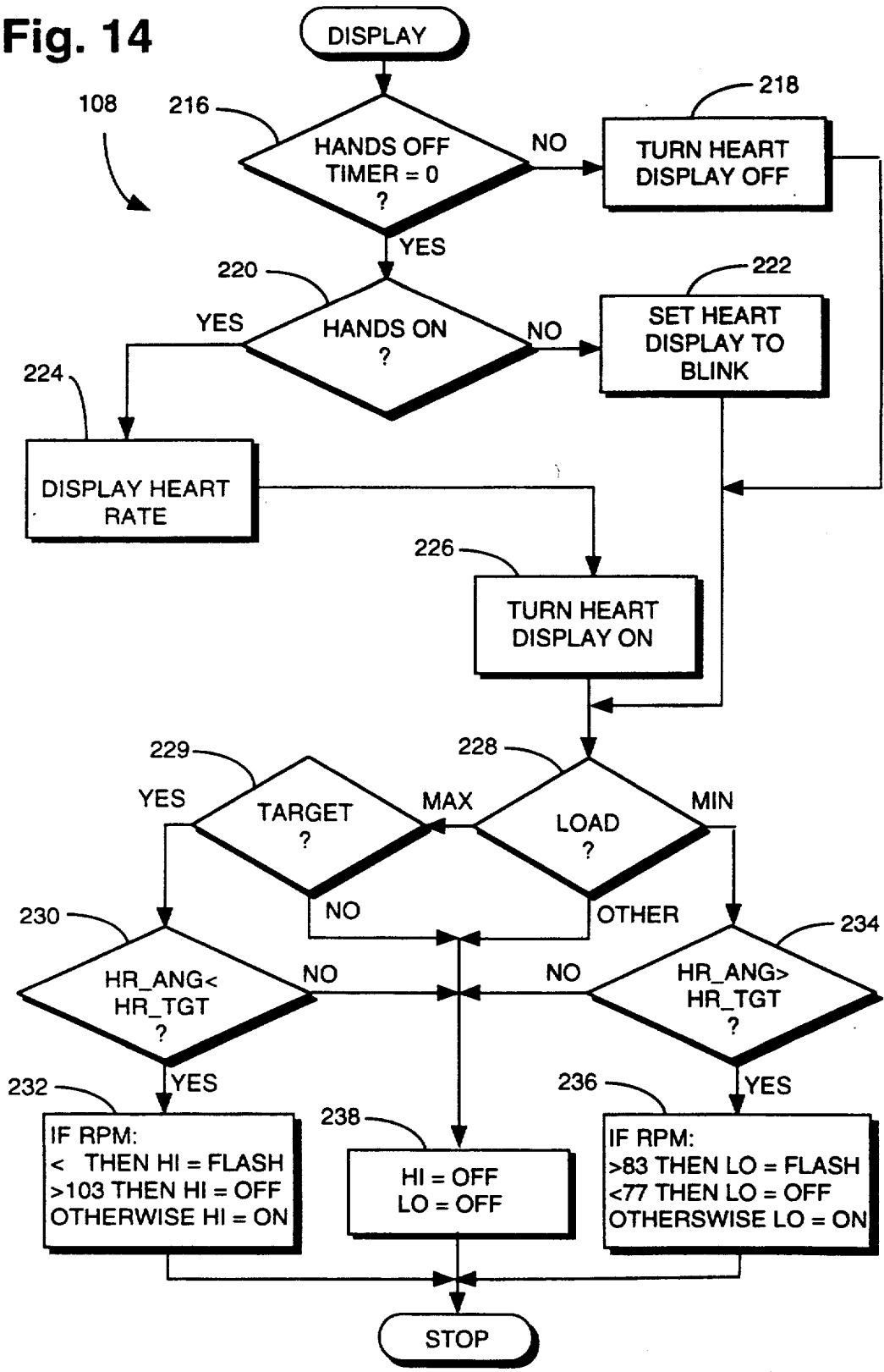

Referring back to FIG. 6, it will be noted that the display module 108 is called with each iteration of the main driver loop 102. The display module manages the display of information to the user via the control panel 30. Referring to FIG. 14, the operation of the display module 108 is illustrated in greater detail. The primary function of the display module 108 is to prompt the user when to place his hands on the pulse sensors 38, and to advise the user when he is free to remove his hands.

As shown in blocks 216-222, the microcomputer 54 initially determines whether the hands-off timer has a value equal to zero (HR_TMR=0). It will be recalled that the hands-off timer is set by the load control module 106 (discussed above in connection with FIG. 12) to specify periods when the user is free to remove his hands from the sensors 38. Thus, when the hands-off timer is at zero, the hands-off period is over. The system 52 requires additional heart rate data, and it is time for the user to place his hands back on the sensors 38. If the hands-off timer is not at zero, then the system 52 does not yet require current heart rate data. Microcomputer 54 turns off the LED heart screen, as shown in the block 218, thereby advising the user that he is free to remove his hands from the sensors.

If the hands-off timer is equal to zero, the microcomputer determines if a hands-on condition exists, as shown at the block 220. If the user's hands are not on the sensors 38, microcomputer 54 sets the LED heart screen 76 to blink, as shown at the block 222. The microcomputer 54 also disables the heart-shaped LED hands-on indicator 78 and clears the LED heart rate display 74. This prompts the user to place his hands on the pulse sensors 38. If, however, the user's hands are already on the sensors 38, then the microcomputer enables the LED hands-on indicator 78, displays the current value of heart rate (HR_NEW) or the "Hr" symbol on the LED heart rate display 74, and turns on the LED heart screen. It may also be desirable to display the user's heart rate whenever the user touches the pulse sensors, regardless of whether the hands-off timer is zero.

As shown in blocks 228-236, the display module also examines the value of load resistance (LOAD), and determines whether load is at the value of the soft maximum (SOFT_MAX), or at the value of zero, as shown at the block 228. If the load resistance is equal to the soft maximum, then the TARGET flag is examined at the block 229 to determine if the user has ever reached the target heart rate. If TARGET is false, then the display module terminates. Otherwise, if TARGET is true, then current heart rate is examined to determine if it is less than the target heart rate, as shown in the block 230. If the user has reached the target heart rate, the display module terminates. Otherwise, the current value of rpm is examined, as shown by the block 230. As illustrated at the block 232, if the user's rpm is below 103, then the high rpm LED 80 is enabled. This prompts the user to maintain a pedal rpm near the high level of 100 (indicated by the indicia 92 on panel 30, as shown in FIG. 5). If the user's rpm level is below 98, then the high rpm LED is set to blink so as to prompt the user to increase pedal rpm to 100.

Contrastingly, if the load resistance is at a minimum, and the user's heart rate is at or below the target heart rate, then the display module terminates, as shown by the block 234. However, if the user's heart rate is above the target heart rate, then the current value of rpm is examined, as shown by the block 234. As illustrated at the block 236, if the user's rpm is above 82 then the low rpm LED 82 is set to blink. This prompts the user to reduce pedal rpm to the low rpm level of 80 (indicated by the indicia 94 on panel 30, as shown in FIG. 5). If the user's rpm level is between 77 and 82, the low rpm LED 82 is turned on. This prompts the user to maintain pedal rpm near 80 rpm. If the user's rpm is below 77, the low rpm LED 82 is turned off.

4. Safety Module

Referring back to FIG. 6, it will be noted that the safety module 110 is called with each iteration of main driver loop 102. The function of the safety module is to ensure that the system 52 does not continue to operate without sufficient heart rate data. Unlike some existing systems, the safety features of the present invention do not disable the bicycle 20 or even warn the user when the user's heart rate reaches a critical level. Rather, the safety features of the present invention take effect when there is an absence of new heart rate data for a prolonged period of time.

Figure 15:
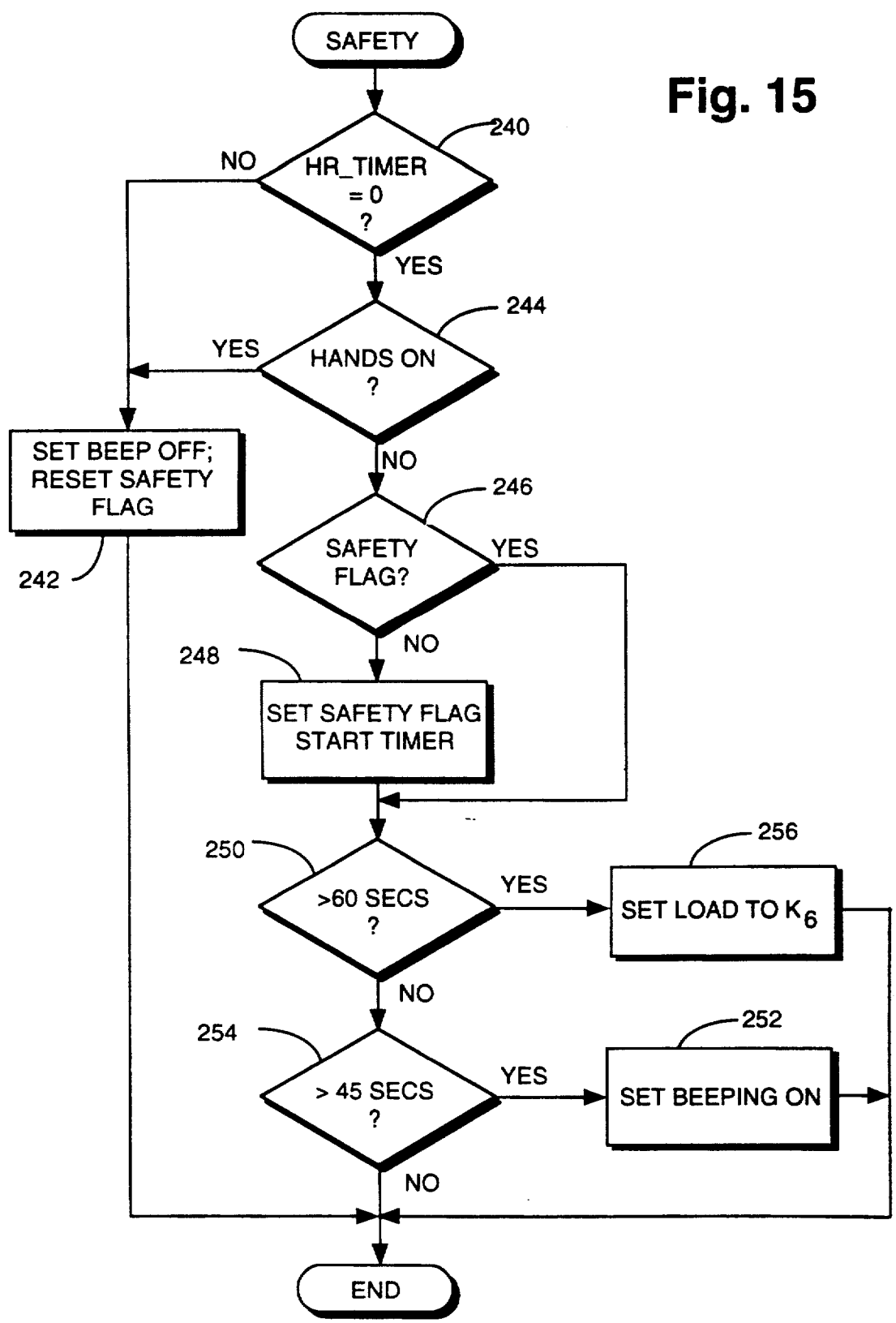

The operation of the safety module 11? is illustrated in greater detail by FIG. 15. As shown in a block 240, the microcomputer 54 determines whether the hands-off timer (HR_TMR) is currently set to zero. If not, then it is permissible for the user to have his hands off of the sensors 38, and no further action is necessary. The safety module disables the bell 85, as shown at a block 242, and terminates.

If, however, the hands-off timer is equal to zero, then the hands-on signal is examined, as shown in a block 244. If the hands-on signal indicates a hands-on condition, then the safety module disables the bell 85, as shown at block 242, and terminates.

If instead the hands-off timer is zero *and* the user's hands are off, the safety module sets a safety flag and starts a safety timer, as shown in blocks 246 and 248. The safety timer may be implemented using timer 60 of microcomputer 54 in any suitable manner, and in practice is a counter that is periodically incremented by a timer interrupt. The safety timer should not be confused with the hands-off timer.

During this and each subsequent iteration of the safety module 110, the value of the safety timer is examined, as shown in blocks 250–256. When the timer reaches 45 seconds, the microcomputer 54 enables the bell 85, as shown in the block 252. The beeping sound augments the flashing LED heart screen (set by the display module 108) to advise the user to place his hands on the pulse sensors 38. If the user does not place his hands on the pulse sensors 38, the safety flag will remain on, and the timer will continue to increment. If the timer reaches sixty seconds, the load resistance is set to a predetermined value K₆, which may be zero or other low value of load, as shown in the block 256, to provide the user with additional incentive to place his hands on the sensors 38, and to reduce the risk that the user may attain an excessive heart rate.

It will be noted that when the user places his hands on the sensors 38, the safety flag is reset on the next iteration of the safety module, as shown in the block 242.

We claim:

1. An exercise management system for maintaining a user's level of exercise intensity at a target level while exercising, comprising:
   (a) movement means adapted for engagement by the user for providing the user with an exercise movement, said movement means being selectively adjustable for varying the intensity of exercise performed by the user;
   (b) sensor means adapted for intermittent engagement with the user for detecting a physiological condition of the user and generating a signal indicating the user's level of exercise intensity based on said physiological condition; and
   (c) control means operatively associated with said movement means and said sensor means for adjusting said movement means in accordance with said signal to establish and maintain the user's exercise intensity near the target level; and maintaining the user's level of exercise intensity near said target level during periods when the user is disengaged from said sensor means.

2. The exercise management system according to claim 1 further comprising a display operatively associated with said control means for inviting the user to disengage said sensor means for a time period once the user's level of exercise intensity reaches the target level.

3. The exercise management system according to claim 2 further comprising rate measuring means for measuring the user's rate of exercise, wherein said control means is responsive to said rate measuring means for maintaining the user's exercise intensity near the target level.

4. The exercise management system according to claim 3 wherein said movement means comprises pedals, and said rate measuring means measures the rate of exercise by measuring the rotational speed of said pedals.

5. The exercise management system according to claim 3 wherein said movement means comprises a treadmill having an endless belt, and said rate measuring means measures the rate of exercise by measuring the speed of said endless belt.

6. The exercise management system according to claim 3 wherein said movement means comprises a frame having vertically reciprocating pedals upon which the user stands to simulate stair climbing, and said rate measuring means measures the rate of exercise by measuring the rate at which said pedals reciprocate.

7. The exercise management system according to claim 2 wherein the duration of said time period is a function of the user's level of exercise intensity.

8. The exercise management system according to claim 2 wherein said display means includes prompting means for prompting the user to reengage said sensor means when said time period has expired.

9. The exercise management system according to claim 8 further comprising means for detecting whether the user is engaged with said sensor means; and alarm means operatively associated with said detecting means for alerting the user if the user has not reengaged said sensor means within a predetermined amount of time after said time period has expired.

10. An exercise apparatus for maintaining a user's level of exercise intensity near a target level while exercising, comprising:
   (a) movement means for engaging the user in an exercise movement, said movement means being selectively adjustable in response to a load signal for varying the intensity of exercise performed by the user;
   (b) physiological sensor means engaged with the user for sensing a physiological condition of the user and generating a physiological signal indicating the user's physiological exercise intensity;
   (c) rate sensor means for generating a rate signal indicating the user's rate of said exercise movement; and
   (d) control means responsive to said physiological and rate signals for generating said load signal in accordance with said physiological and rate signals to establish and maintain the user's exercise intensity near the target; wherein said control means varies said load signal in accordance with said rate signal only after said physiological signal indicates that the user's level of exercise intensity has reach the target level.

11. The exercise apparatus according to claim 10 wherein said control means varies said load signal to increase intensity of exercise in response to said rate signal indicating a decreasing rate of exercise.

12. The exercise apparatus according to claim 10 wherein said control means varies said load signal to decrease the intensity of exercise in response to said rate signal indicating an increasing rate of exercise.

13. The exercise apparatus according to claim 10 further comprising display means for:
periodically inviting the user to disengage said physiological sensor means once the user's level of exercise intensity reaches the target level;
prompting the user to engage said physiological sensor means after the user has disengaged said physical sensor means for a preselected time period; and
wherein said control means varies said load signal in response to said rate signal while the user has disengaged said physiological sensor means to maintain the user's level of exercise intensity near the target level.

14. The exercise apparatus according to claim 13 further comprising means for detecting whether the user is engaged with said physiological sensor means; and alarm means operatively associated with said detecting means for alerting the user if the user has not re-engaged said physiological sensor means within a predetermined amount of time after said preselected time period has expired.

15. An exercise apparatus for maintaining a user's heart rate near a preselected target rate while exercising, comprising:
(a) movement means adopted for engagement by a user for providing the user with an exercise movement;
(b) resistance means for applying a variable level of resistance in opposition to said exercise movement, said resistance means being selectively adjustable in response to a load control signal for varying said level of resistance;
(c) a first sensor adapted for engagement with the user for generating a heart rate signal representing the user's heart rate;
(d) a second sensor operatively associated with said movement means for generating an exercise rate signal representing the rate of said exercise movement; and
(e) load control means for generating said load control signal in accordance with said heart rate signal to establish the user's heart rate at a level near the target rate and for generating said load control signal in accordance with said heart rate signal and said exercise rate signal once the user's heart rate is established at a level near the target rate to maintain the user's heart rate near the target rate.

16. The exercise apparatus according to claim 15 wherein:
said movement means comprises pedals;
said second sensor measures the rate of exercise movement by measuring the rotational speed of said pedals; and
said resistance means applies a variable level of resistance in opposition to the movement of said pedals.

17. The exercise apparatus according to claim 15 wherein:
said movement means comprises a treadmill having an endless belt that defines an exercise surface;
said second sensor measures the rate of exercise movement by measuring the speed of said endless belt; and
said resistance means includes means for positioning said exercise surface at varying degrees of incline relative to the horizontal to vary said level of resistance.

18. The exercise apparatus according to claim 15 wherein:
said movement means comprises a frame having vertically reciprocating pedals upon which the user stands to simulate stair climbing; and
said second sensor measures the rate of exercise movement by measuring the rate at which said pedals reciprocate.

19. The exercise apparatus according to claim 18 wherein said resistance means applies a variable level of resistance in opposition to the movement of said pedals.

20. The exercise apparatus according to claim 18 wherein said resistance means varies the vertical distance over which said pedals reciprocate to vary said level of resistance.

21. The exercise apparatus according to claim 15 wherein said load control means varies said load control signal to increase said level of resistance in response to said exercise rate signal indicating a decreasing rate of exercise, and to decrease said level of resistance in response to said exercise rate signal indicating increasing rate of exercise.

22. The exercise apparatus according to claim 4 further comprising:
means for inviting the user to disengage said first sensor once the user's heart rate reaches the target rate; and
means operatively associated with said load control means for detecting when the user has disengaged said first sensor;
wherein said load control means varies said load control signal in response to said heart rate signal to maintain the user's heart rate near the target rate when the user has disengaged said first sensor.

23. The exercise apparatus according to claim 22 further comprising:
means for selecting a time period in accordance with predetermined criteria, said time period being measured from when the user disengages said first sensor in response to said inviting means; and
means for prompting the user to reengage said first sensor after the expiration of said selected time period.

24. The exercise apparatus according to claim 23 wherein said predetermined criteria include whether the user's heart rate is approaching the target.

25. The exercise apparatus according to claim 23 wherein said prompting means prompts the user to reengage said first sensor prior to the expiration of said selected time period if the change over time in said rate of exercise movement exceeds a predetermined threshold.

26. The exercise apparatus according to claim 23 further comprising alarm means operatively associated with said detecting means for alerting the user if the user has not re-engaged said first sensor within a predetermined time after said selected time period has expired.

27. The exercise apparatus according to claim 23 further comprising means for reducing said level of resistance to a predetermined level if the user has not re-engaged said first sensor within a predetermined time after said selected time period has expired.

28. An exercise management system for maintaining a user's heart rate near a target heart rate during exercise on an exercise apparatus having movement means adapted for manipulation by the user in an exercise movement and an adjustable load device for applying a selectively variable level of resistance in opposition to the exercise movement, comprising:
 (a) first sensor means adapted for engagement with the user for generating a heart rate signal representing the user's heart rate;
 (b) second sensor means operatively associated with said movement means for generating an exercise rate signal representing the rate of said exercise movement; and
 (c) control means coupled to said first and second sensor means for
  adjusting the load device in accordance with said heart rate signal to establish and maintain the user's heart rate near the target heart rate;
  periodically inviting the user to disengage said first sensor means for a time period of selected duration; and
  adjusting the load device in accordance with said exercise rate signal during said time period when the user has disengaged said first sensor means to maintain the user's heart rate near said target heart rate.

29. The exercise management system according to claim 4 wherein said control means further comprises memory means for recording the value of said heart rate signal at a first and a subsequent time;
 wherein said control means adjusts the load device to vary the level of resistance by an amount equal to:

$$(D\_TARGET - D\_HEART) * K;$$

wherein D_TARGET is the difference of the target heart rate minus the average value of said heart rate signal at said first and subsequent times, and D_HEART is equal to the value of said heart rate signal at said subsequent time minus the value of said heart rate signal at said first time; and
 wherein K is a predetermined scaling constant.

30. The exercise management system according to claim 28 wherein said control means limits the adjustment to the load device signal so that the change in the level resistance with respect to time does not exceed a predetermined maximum.

31. The exercise management system according to claim 28 wherein said control means further comprises memory means for recording the value of said heart rate signal at a first and a subsequent time;
 wherein said control means selects the duration of said time period as a function of the difference between D_TARGET and D_HEART;
 wherein D_TARGET is equal to the target heart rate minus the average value of said heart rate signal at said first and subsequent times, and D_HEART is equal to the value of said heart rate signal at said subsequent time minus the value of said heart rate signal at said first time.

32. The exercise management system according to claim 28 further comprising means for prompting the user to re-engage said first sensor means after the expiration of said time period.

33. The exercise apparatus according to claim 28 further comprising detecting means operatively associated with said first sensor means for detecting when the user has disengaged said first sensor means, and alarm means operatively associated with said detecting means for alerting the user when the user has not re-engaged said first sensor means within a predetermined time after said selected time period has expired.

34. The exercise apparatus according to claim 28 further comprising detecting means operatively associated with said first sensor means for detecting when the user has disengaged said first sensor means, and means operatively associated with said detecting means for reducing said level of resistance to a predetermined level in response to the user not re-engaging said first sensor means within a predetermined time after said selected time period has expired.

35. An exercise apparatus for maintaining a user's heart rate near a preselected target while exercising, comprising:
 (a) movement means for engaging the user in an exercise movement, said movement means being adjustable for selectively applying a level of resistance in opposition to said exercise movement, said level of resistance being variable within a range;
 (b) sensor means engaged with the user for generating a heart rate signal representing the user's heart rate;
 (c) level selection means operatively associated with said movement means for enabling the user to select a maximum level of resistance within said range; and
 (d) control means responsive to said heart signal, said level selection means, and said movement means for adjusting said level of resistance in accordance with said heart rate signal to establish and maintain the user's heart rate near the target; said control means further including means for maintaining said level of resistance below a variable soft maximum value that is a function of the said user-selected maximum level of resistance.

36. The exercise apparatus according to claim 35 wherein said control means increments said soft maximum value by a predetermined amount when:
 said level of resistance is equal to said soft maximum value;
 greater resistance is required to establish and maintain the target heart rate; and
 said heart rate signal indicates that the user's heart rate is not increasing with respect to time.

37. The exercise apparatus according to claim 36 wherein said control means does not increase said soft maximum value when said soft maximum value equals a predetermined hard maximum value that is a function of said user-selected level of resistance.

38. The exercise apparatus according to claim 35 further comprising:
 a second sensor operatively associated with said movement means for generating a rate signal representing the rate of said exercise movement;
 display means for prompting the user to engage in a faster rate of said exercise movement when said rate of exercise movement is below a predetermined rate, said heart rate signal indicates that the user's heart rate is below the target, and said level of resistance is equal to said soft maximum value.

39. The exercise apparatus according to claim 35 further comprising:
   a second sensor operatively associated with said movement means for generating a rate signal representing the rate of said exercise movement;
   display means for prompting the user to engage in a slower rate of said exercise movement when said rate of exercise movement is above a predetermined rate, said heart rate signal indicates that the user's heart rate is above the target, and said level of resistance is at the lowest level of said range.

40. A method for maintaining a user's level of exercise intensity at a target level while exercising on an exercise apparatus having movement means for providing the user with a exercise movement of selectively variable intensity, comprising the steps of:
   (a) periodically measuring the user's level of physiological exercise intensity;
   (b) periodically measuring the user's rate of exercise movement;
   (c) adjusting the movement means in accordance with the measured level of physiological exercise intensity to establish and maintain the user's physiological exercise intensity near the target level; and
   (d) adjusting the movement means in accordance with the measured rate of exercise movement once the user's physiological exercise intensity has reached the target level.

41. The method according to claim 40 wherein the step of measuring physiological exercise intensity is performed intermittently once the user's physiological exercise intensity has reached the target level, the duration of intervals between the intermittent measurements being a function of the user's level of physiological exercise intensity.

42. A method for maintaining a user's heart rate at a target level while exercising on an exercise apparatus having movement means for providing the user with an exercise movement of selectively adjustable intensity, comprising the steps of:
   (a) periodically measuring the user's heart rate;
   (b) adjusting said movement means in accordance with the measured heart rate to establish and maintain the user's heart rate at the target level;
   (c) once the user's heart rate reaches the target level suspending the measurement of the user's heart rate for a selected time period;
   (d) periodically measuring the rate of said exercise movement;
   (e) during said selected time period when measurement of the user's heart rate is suspended, adjusting said movement means in accordance with the measured rate of exercise movement to maintain said heart rate at the target level.

43. The method according to claim 42 wherein said step of adjusting said movement means in accordance with the measured heart rate comprises the steps of:
   subtracting an earlier measured heart rate from the most recently measured heart rate to determine an actual change in heart rate over time;
   subtracting the most recently measured heart rate from the target hear rate to determine a desired change in heart rate;
   subtracting said actual change in heart rate from said desired change in heart rate to determine an adjustment value; and
   adjusting said movement means in accordance with said adjustment value.

44. The method according to claim 43 further comprising the step of reducing the duration of said selected time period when the change in the measured rate of exercise movement over time exceeds a predetermined threshold.

45. The method according to claim 42 further comprising the step of computing the duration of said selected time period as a function of the user's measured heart rate and the target heart rate.

46. A method for maintaining a user's heart rate at a target level while exercising on an exercise apparatus having movement means for providing the user with an exercise movement of selectively variable intensity, comprising the steps of:
   (a) engaging a sensor to the user to sample the user's heart rate;
   (b) adjusting said movement means in accordance with said sampled heart rate to establish said heart rate near the target level; and
   (c) once the user's heart rate reaches the target level, sampling the user's rate of exercise movement and adjusting said movement means in accordance with said sampled rate of exercise movement to maintain the user's heart rate near the target level for a selected time period.

47. The method according to claim 46 wherein the duration of said selected time period is a function of the user's heart rate.

* * * * *